US007011631B2

(12) United States Patent
Davis et al.

(10) Patent No.: US 7,011,631 B2
(45) Date of Patent: Mar. 14, 2006

(54) NONINVASIVE METHOD OF MEASURING BLOOD DENSITY AND HEMATOCRIT

(75) Inventors: Charles L. Davis, Beaverton, OR (US); Patrick D. Harrison, Seattle, WA (US); John E. Bronson, Keizer, OR (US)

(73) Assignee: Hemonix, Inc., Beaverton, OR (US)

( * ) Notice: Subject to any disclaimer, the term of this patent is extended or adjusted under 35 U.S.C. 154(b) by 190 days.

(21) Appl. No.: 10/760,625

(22) Filed: Jan. 20, 2004

(65) Prior Publication Data

US 2004/0249292 A1 Dec. 9, 2004

Related U.S. Application Data

(60) Provisional application No. 60/441,630, filed on Jan. 21, 2003.

(51) Int. Cl.
  *A61B 5/00* (2006.01)
(52) U.S. Cl. .............. 600/368; 600/309; 600/507; 600/547
(58) Field of Classification Search ............. 600/368
See application file for complete search history.

(56) References Cited

U.S. PATENT DOCUMENTS

| | | | |
|---|---|---|---|
| 3,769,834 A | 11/1973 | Fletcher et al. | |
| 3,957,197 A | 5/1976 | Sartory et al. | |
| 3,998,550 A | 12/1976 | Konishi et al. | |
| 4,169,463 A | 10/1979 | Piquard | |
| 4,178,918 A | 12/1979 | Cornwell | |
| 4,204,545 A | 5/1980 | Yamakoshi | |
| 4,407,290 A | 10/1983 | Wilber | |
| 4,524,777 A | 6/1985 | Kisioka et al. | |
| 4,547,735 A | 10/1985 | Kiesewetter et al. | |
| 4,548,211 A * | 10/1985 | Marks .................. | 600/507 |
| 4,745,279 A | 5/1988 | Karkar et al. | |
| 4,873,987 A | 10/1989 | Djordjevich et al. | |
| 4,875,488 A * | 10/1989 | Shimazu et al. ............ | 600/507 |

(Continued)

FOREIGN PATENT DOCUMENTS

WO 02/24053 3/2002

OTHER PUBLICATIONS

H. Shimazu et al., *Electric Impedance Cuff For The Indirect Measurement Of Blood Pressure And Volume Elastic Modulus In Human Limb And Finger Arteries*, Medical & Biological Engineering & Computing (1989), pp. 477-483.

(Continued)

*Primary Examiner*—Robert L. Nasser
*Assistant Examiner*—Patricia Mallari
(74) *Attorney, Agent, or Firm*—Pauley Petersen & Erickson

(57) ABSTRACT

Apparatus and methods for noninvasively measuring blood density and hematocrit in a human subject can include an appliance for applying pressure around a segment of a subject's limb or appendage that includes a pressure sensing means and encloses an array of impedance sensing devices applied to the subject's skin for independent fluid volume measurements. While applying pressure to the limb segment by the pressure appliance, measurements of blood pressure, blood pulse wave velocity, and limb segment impedance are recorded. The measurements are subsequently processed to yield changes of arterial blood volume during pulse wave passage. Then pressure, wave velocity, and derived volume data are combined to yield the density of the blood. Blood density is converted to hematocrit by means of a linear relationship between the two. Independent of the blood hematocrit, such apparatus and means may also be used to measure the density of enclosed fluid in other pulsed flow non-rigid wall vessel systems.

19 Claims, 16 Drawing Sheets

U.S. PATENT DOCUMENTS

| | | |
|---|---|---|
| 4,927,264 A | 5/1990 | Shiga et al. |
| 5,090,417 A | 2/1992 | Mollan et al. |
| 5,101,825 A | 4/1992 | Gravenstein et al. |
| 5,237,997 A | 8/1993 | Greubel et al. |
| 5,241,963 A | 9/1993 | Kung et al. |
| 5,277,181 A | 1/1994 | Mendelson et al. |
| 5,309,916 A | 5/1994 | Hatschek |
| 5,343,868 A | 9/1994 | Kurscheidt et al. |
| 5,351,686 A | 10/1994 | Steuer et al. |
| 5,351,694 A | 10/1994 | Davis et al. |
| 5,372,136 A | 12/1994 | Steuer et al. |
| 5,400,793 A | 3/1995 | Wesseling |
| 5,423,322 A | 6/1995 | Clark et al. |
| 5,423,324 A | 6/1995 | Tomita |
| 5,447,161 A | 9/1995 | Blazek et al. |
| 5,456,253 A | 10/1995 | Steuer et al. |
| 5,487,384 A | 1/1996 | Lee |
| 5,499,627 A | 3/1996 | Steuer et al. |
| 5,526,808 A | 6/1996 | Kaminsky |
| 5,553,615 A | 9/1996 | Carim et al. |
| 5,564,418 A | 10/1996 | Ozaki et al. |
| 5,566,667 A | 10/1996 | Cox |
| 5,630,424 A | 5/1997 | Raines et al. |
| 5,642,734 A | 7/1997 | Ruben et al. |
| 5,692,513 A | 12/1997 | Davis et al. |
| 5,711,303 A | 1/1998 | Shimizu et al. |
| 5,715,828 A | 2/1998 | Raines et al. |
| 5,720,284 A | 2/1998 | Aoyagi et al. |
| 5,724,981 A | 3/1998 | Apple |
| 5,755,226 A | 5/1998 | Carim et al. |
| 5,803,908 A | 9/1998 | Steuer et al. |
| 5,823,045 A | 10/1998 | Van Driel et al. |
| 5,833,602 A | 11/1998 | Osemwota |
| 5,836,317 A | 11/1998 | Kunst |
| 5,978,691 A | 11/1999 | Mills |
| 5,983,120 A | 11/1999 | Groner et al. |
| 6,120,459 A | 9/2000 | Nitzan et al. |
| 6,125,297 A | 9/2000 | Siconolfi |
| 6,128,518 A * | 10/2000 | Billings et al. ............. 600/345 |
| 6,527,728 B1 * | 3/2003 | Zhang ........................ 600/500 |
| 6,554,774 B1 | 4/2003 | Miele |
| 6,561,986 B1 | 5/2003 | Baura et al. |
| 6,640,625 B1 * | 11/2003 | Goodwin ................. 73/152.05 |
| 6,740,036 B1 * | 5/2004 | Lee et al. .................... 600/437 |
| 6,749,567 B1 | 6/2004 | Davis et al. |
| 2003/0135124 A1 | 7/2003 | Russell |

OTHER PUBLICATIONS

H. Shimazu et al., *Evaluation of the Parallel Conductor Theory for Measuring Human Limb Blood Flow by Electrical Admittance Plethysmography*, IEEE Transactions on Biomedical Engineering, 1982, vol. BME-29,. No. 1.

Patrick Zickler: *Bioimpedance Measurements*, Biomedical Instrumentation & Technology, p. 173-175, Mar./Apr. 1998.

Rudolph J. Liedtke, *Bioelectrical Impedance Principles*, Apr. 1997.

Jaap H. J. Muntinga and Klaas R. Visser, *Estimation of blood pressure-related parameters by electrical impedance measurement*, Journal of Applied Physiology, Nov. 1992; 73(5), pp 1946-1957.

P. Gizdulich and K. H. Wesseling, *Forearm arterial pressure-volume relationships in man*, Clin. Phys. Physiol. Meas., 1988, vol. 9, No. 2, pp 123-132.

* cited by examiner

Side view of parallel conductor body segment with $Y_{ca}$, $Y_{bc}$, and $Y_{bv}$ End view of arterial bed segment Cuff Pressure Generator applied to a limb segment

NONINVASIVE METHOD OF MEASURING BLOOD DENSITY AND HEMATOCRIT

This application claims the benefit of provisional application 60/441,630 filed Jan. 21, 2003.

BACKGROUND OF THE INVENTION

1. Field of the Invention

This invention relates to noninvasive determination of fluid density including the density of blood and hematocrit in a living subject.

2. Discussion of the Related Art

Hematocrit, an important clinical parameter, is the ratio of red blood cell volume to whole blood volume, and is often expressed as a fraction or a percent. In current medical practice the hematocrit can only be determined by invasive methods that first require drawing blood from the living subject, and then use a centrifuge or optical instrument on the raw blood to determine the hematocrit value.

Because current hematocrit monitoring techniques are invasive they expose both the caregiver and the patient to the risks of blood-borne diseases such as AIDS and hepatitis. In addition to causing discomfort to the patient and risk to the caregiver, they are also time consuming to administer, and may result in delays in treatment while results are being processed.

The primary current clinical method for determining hematocrit is the centrifuge method, e.g., U.S. Pat. No. 3,957,197. This method requires drawing a blood sample, and relies upon the differences in density of the component parts of blood (red blood cells and plasma). The centrifuge rapidly spins the blood in a tube, causing the denser parts of the blood (red blood cells) to go to the bottom of the tube, and the less dense parts (plasma) to stay near the top of the tube. After a sufficient amount of spin time (usually several minutes) has elapsed during centrifuging of the blood, all of the red blood cells are packed into the bottom of the tube with the plasma riding on top of the cells. If the length of the tube is calibrated to volume percent increments, the clinician can simply read the value of "Packed Cell Volume" from the side of the tube at the top of the cell region. "Packed Cell Volume" is slightly different from "hematocrit," since the method of centrifuging does not perfectly pack the cells into the bottom of the tube. This leaves small spaces within the cell area of the tube for plasma to reside, resulting in an approximate 4% to 5% error between the Packed Cell Volume and the true hematocrit value. However, clinicians generally use Packed Cell Volume and Hematocrit synonymously.

Discussion of the Related Art for Non-Invasive Hematocrit

Various inventions have been disclosed, e.g., U.S. Pat. Nos. 5,978,691; 5,983,120; 5,836,317; 5,833,602; 5,803,908; 5,755,226; 5,720,284; 5,642,734; 5,564,418; 5,553,615; 5,526,808; 5,499,627; 5,487,384; 5,456,253; 5,372,136; 5,351,686; 5,277,181, and 5,101,825, which describe methods for measuring the hematocrit by noninvasive means. No noninvasive hematocrit monitor has yet become commercially available. Four basic methods have been disclosed in the art for noninvasively measuring hematocrit in a living body;

1) Optical sensing of the hemoglobin versus methemoglobin and plasma. This technique measures the relative extinction coefficients at various wavelengths of light to determine the concentration of hemoglobin versus other constituent parts of whole blood (U.S. Pat. Nos. 5,833,602 and 5,803,908);

2) Impedance sensing of the body at various select frequencies. The change of impedance values from low to high frequencies determines hematocrit from the relationship of those values (U.S. Pat. Nos. 4,547,735 and 5,526,808);

3) Reflected Imaging Analysis. This technique visually counts red blood cells in the vessel of a patient in-vivo, and determines the hematocrit by volume analysis (U.S. Pat. No. 5,983,120);

4) Mass change in hemoglobin resulting from a measured change in volume of blood (U.S. Pat. No. 5,101,825).

Each of these methods measures attributes of component parts of the blood in-vivo and calculates the hematocrit from the relative values obtained. None of the prior art methods noninvasively determine the density of the whole blood in-vivo.

Method 1 has as confounding factors the variances in light extinction due to fluid volume and skin pigmentation that adversely affect the accuracy and repeatability of the method. Method 2 uses the variation of complex impedance versus frequency to determine the relative concentration of Erythrocytes to whole blood. The confounding factor of this method is the variability of Erythrocyte cell wall thickness across a population of healthy and unhealthy patients. Since the complex impedance method is dependent on the cell wall capacitance, any variation in mean cell wall thickness has a marked affect on the total capacitance contributed by any single cell in solution. Variations in capacitance versus frequency are affected by various disease states of the patient and will contribute substantially to the inaccuracy of the measurement for these patients. Method 3, e.g., U.S. Pat. No. 5,983,120, is mechanically cumbersome to apply to the patient since the probe must be applied under the tongue of the patient for an extended period of time in order to make the measurement. This method is discomforting to a broad population of patients. Method 4, e.g., U.S. Pat. No. 5,101,825, has difficulty calibrating to the patient since the value of $\Delta V$ (the change in blood volume over time) is difficult to quantify by optical means.

SUMMARY OF THE INVENTION

The present invention provides means and methods for noninvasively determining the fluid density in a pulsed flow system with non-rigid wall vessels such as found in the vascular system of living subjects. In humans and other pulse flow mammals this fluid density is the blood density of the subject. Other fluids, semi-fluids, or materials which can be moved by a pulsed flow system may be measured. This invention makes use of noninvasive measurements of fluid pressure, fluid volume, and fluid pulse wave velocity to determine the fluid density and when the fluid is blood, a further method is disclosed which allows the determination of the hematocrit of the blood from the blood density value. The primary application of this invention is the noninvasive measurement of hematocrit and blood density in humans and animals but it is anticipated by the inventors that the methods disclosed herein will apply to any pulsed flow system with non-rigid wall vessels.

The general advantages of noninvasive measurement of hematocrit compared to current practices of invasive measurement include a reduced risk of contracting blood-borne diseases for care givers and patients, elimination of patient risk of infection, clotting, and blood vessel damage, early warning of impending Shock condition that will help save lives now lost, lower cost of procedures, less time consumption per procedure for clinicians, increased speed and repeatability of measurements that improves the reporting of results, and reduction in patient discomfort.

Specific users of the present invention may include ambulances, trauma/emergency care centers, military field operations, surgery, hemodialysis, blood banks, and Ob/Gyn.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION

Figure 1:
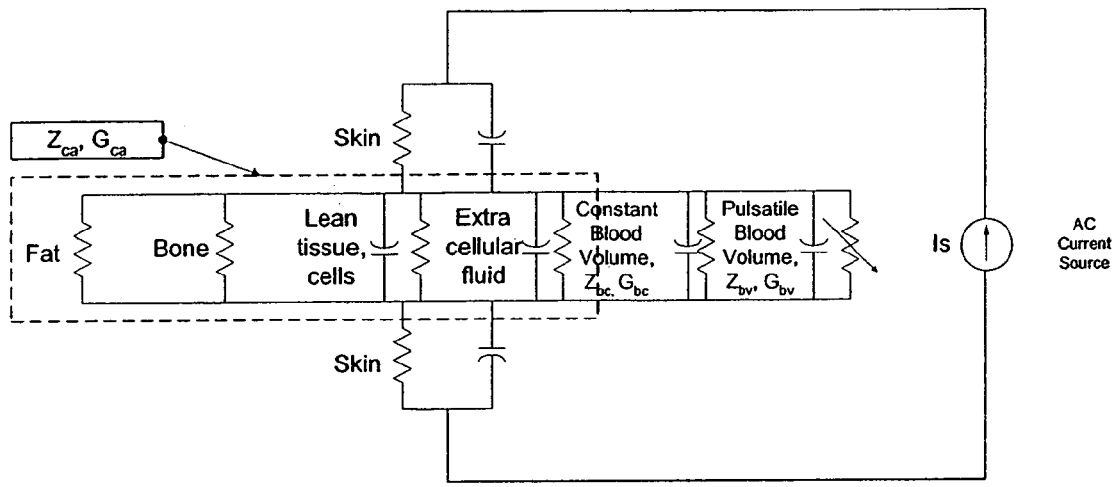
FIGS. 1 and 2 depict equivalent circuit models of the body given by parallel conductor theory.

The present invention provides means and methods for noninvasively determining the fluid density in a pulsed flow system with non-rigid wall vessels such as found in the vascular system of living subjects. Thus the detailed description focuses on the exemplary embodiment of finding blood density, and further calculating a hematocrit value from the blood density. It will be appreciated that the sphere of the present invention need not be limited strictly to vascular blood systems.

Two technology areas can be useful in the practice of the exemplary embodiment of the present invention: electrical modeling of the human body, and pulse wave propagation models of the human circulatory system. The first postulates a model of the human body in terms of its electrical behavior, and relates physiological changes to changes in that electrical behavior. The second describes pressure wave propagation in the arteries in terms of blood volume changes.

Electrical Models of the Human Body

The "Parallel Conductor Theory" describes the human body as composed of various conductive elements that represent different materials of the human body composition.

The electrical impedance, Z of a body component (bone, fat, muscle, blood, etc.) is a complex number, $Z=R+jX$, characterized by its resistance R and reactance X. The admittance, Y, of this component the inverse of the impedance, or $1/Z$. The impedance, Z, of a column of material with a cross sectional area $A_{cs}$ (cm$^2$) and length l (cm) is:

$$Z = \frac{\rho_r * l}{A_{cs}} \quad \text{(Impedance form)} \quad \{1\}$$

$$Y = \frac{A_{cs}}{\rho_r * l} \quad \text{(Admittance form)} \quad \{2\}$$

where $\rho_r$ is the bulk resistivity of the measured material in ohm-cm.

In the parallel conductor hypothesis, a limb, or body segment, is equated to a series of parallel conductors in which the volume of blood in the limb is the only variable. The impedance of the whole limb is the sum of the several parallel impedances, $Z_i$, of its components, calculated according to the formula:

$$1/Z=1/Z_1+1/Z_2+1/Z_3 \ldots +1/Z_n$$

but this relation is more easily expressed in terms of admittances of the limb components:

$$Y=Y_1+Y_2+Y_3 \ldots +Y_n$$

The parallel conductor model (FIGS. 1, 2 and 3) is composed of three basic admittance values ($Y_{ca}$, $Y_{bc}$ and $Y_{bv}$). $Y_{ca}$ represents all non-blood elements in the body segment that are unchanging over the span of a cardiac cycle, $Y_{bc}$ represents the basal, or constant, blood admittance in the segment over the cardiac cycle, and $Y_{bv}$ represents the variable blood admittance. '$Y_c$ represents the sum of $Y_{ca}$ and $Y_{bc}$ and is the total portion of the segment admittance that does not vary; $Y_b$ is the combination of $Y_{bc}$ and $Y_{bv}$ and represents the total blood admittance; and $Y_t$ is the sum of all three basic admittances and is the total measured segmental admittance. The parallel conductor model can be expressed to show the total admittance of a body segment as;

$$1/Z_t=1/Z_{bv}+1/Z_c \text{ (Impedance form)} \quad \{3\}$$

$$Y_t=Y_{bv}+Y_c \text{ (Admittance form)} \quad \{4\}$$

It has been shown by Jan Nyboer that the arterial blood volume is proportional to the electrical conductance (1/R) in a section of the human body. Nyboer, Jan, *Electrical Impedance Plethysmography*, 2$^{nd}$ Edition, Thomas Books, Springfield, Ill., 1970. This proportionality is dependent on the relationship between the volumetric changes occurring in the vascular bed due to the "pressure wave" caused by the heartbeat and the conductance or impedance value of the vasculature versus time. The ability to accurately and non-invasively measure volumetric changes in the vascular bed by impedance or conductance has been researched and discussed in the literature, e.g., Geddes, L A; and Sadler, C., *"The Specific Resistance Of Blood At Body Temperature*, Med. Biol. Eng. 11(3):336–339, 1973. Shankar, T. M. Ravi; Webster, John G.; and Shao, Shu-Yong; *The Contribution of Vessel Volume Change and Blood Resistivity Change to the*

*Electrical Impedance Pulse*, IEEE Transactions on Biomedical Engineering, Vol. BME-32, No.3, March 1985. *Handbook of Biological Data*, The National Academy of Sciences, National Research Council, Spector, W. S., Ed., W B Saunders, 1956. H. Shimazu, K. Yamakoshi, T. Togawa, M. Fukuoka, *Evaluation of Parallel Conductor Theory for Measuring Human Limb Blood Flow by Electrical Admittance Plethysmography*, January 1981, IEEE Transactions on Biomedical Engineering. *Encyclopedia of Medical Devices and Instrumentation*, John G. Webster, Editor in Chief, Volume 3, pg 1633, 1988, John Wiley & Sons, New York. Nyboer, Jan, *Electrical Impedance Plethysmography*, supra. Lifshitz, K. *Electrical Impedance Cephalography, Electrode Guarding And Analog Study*, Ann. N. Y. Acad. Sci. 170:532–549, 1970.

As shown below, all of these approaches require knowledge of the resistivity of the blood. Nyboer was the first to apply the formula for the resistance of a homogeneous volume conductor to predict the relationship between impedance changes and blood volume changes. Nyboer, J., "*Electrical Impedance Plethysmography: A Physical And Physiologic Approach To Peripheral Vascular Study*, Circulation, 2:811–821, 1950. The electrical impedance $Z_t$ of a cylindrical body segment, such as a limb, can be expressed in terms of its cross sectional area $A_{cs}$, voltage electrode separation L, and tissue resistivity $\rho_{rt}$ $$Z_t = \frac{\rho_{rt} * L}{A_{cs}} \quad \{5\}$$

Since the volume of a body segment, $V_t = L A_{cs}$, electrical resistance can be expressed in terms of the segmental volume, $$Z_t = \frac{\rho_{rt} * L^2}{V_t} \quad \{6\}$$

$$V_t = \frac{\rho_{rt} * L^2}{Z_t} \quad \{6a\}$$

Nyboer further assumed that the segmental blood volume change $\Delta V_{bv}$ could be modeled as the resistance change $\Delta Z_t$ in the segment due to change in blood volume electrically in parallel with the basal, or constant, tissue impedance $Z_t$. This led to the well-known Nyboer Formula, $$\Delta V_{bv} = -\rho_{rb} * L^2 * \frac{\Delta Z_t}{Z_t^2} \quad \{7\}$$

where $\rho_{rb}$ is the resistivity of blood. Without prior knowledge of this resistivity, either from invasive measurement or assumed values, blood volume changes cannot be calculated from external impedance measurements.

Pulse Wave Propagation Models

The Moens-Korteweg equation, first published in 1878, is the most cited work dealing with pressure wave velocity in an artery. It is given by:

$$v = \sqrt{\frac{E * h}{2 * \rho_b * r_i}} \quad \{8\}$$

where v=pulse wave velocity, E=elastic modulus of the vessel wall, h=vessel wall thickness, $\rho_b$=density of the blood, and $r_i$=the vessel inside radius. The pulse wave velocity is the speed at which the pressure pulse propagates along the vessel.

Bramwell and Hill modified the Moens-Korteweg equation to the form, $$v = \sqrt{\frac{V_b}{\rho_b} * \frac{\Delta P}{\Delta V_b}} \quad \{9\}$$

with v=pulse velocity, $V_b$=basal volume of the blood in a vessel, $\Delta P$=transmural pressure change due to the pulse, $\rho_b$=blood density, and $\Delta V_b$=volume change of the blood in the vessel due to the pulse. Bramwell J. C. and Hill A. V., *The Velocity Of Pulse Wave In Man*, Proc. Soc. Exp. Biol. Med., 1922; 93: 298–306 Here the velocity of the pulse wave is expressed in terms of volume, pressure, and density. Prior investigations into vascular behavior, which use the Moens-Korteweg Equation {8} for vascular modeling, have chosen to insert a nominal or invasively determined value for $\rho_b$ in the use of this equation.

It will be noted that in this document the symbol p is used to refer to both the density of a substance in gm/cm$^3$ and to the resistivity of a substance in $\Omega$*cm. This overlapping of symbols is unfortunate, but dictated by convention. In this document resistivity will always have a first subscript of r, as in $\rho_{rb}$ for the resistivity of blood. Whenever $\rho$ does not have a first subscript of r it refers to density, as in $\rho_b$ for the density of blood.

The prior discussion of the Moens-Korteweg Equation {8} and Bramwell and Hill Equation {9} equations describing the propagation velocity of the pulse wave in arteries (or any other elastic wall vessel), illustrates the co-dependent relationship that exists between the propagation velocity (v) of the pulse wave in such a medium and the density of the fluid or blood ($\rho_b$). Blood density is the value of mass/unit volume of the blood. Since whole blood is a hybrid of red blood cells and plasma, each of which differ in density, the density of whole blood is the composite of the density values of the individual component parts on a volume percentage basis. Since the hematocrit is the ratio of the volume of red blood cells to whole blood volume, the density of blood has a linear relationship to the hematocrit. Therefore, the present invention may embody two steps; 1) determination of the density of the blood, and 2) the conversion of blood density into hematocrit.

Determination of Blood Density

As demonstrated by Bramwell and Hill in Equation {9} the pulse propagation velocity of the pressure pulse wave in the arteries is dependent on the density of the blood (Pb). Since blood is essentially an incompressible fluid, the pressure wave propagation is mediated by the effective compressibility of the system provided by the elasticity or compliance of the non-rigid vessel (arterial) wall. This elasticity allows local relative blood volume changes ($V_b/\Delta V_b$) as the pressure wave propagates along the artery. If the pulse wave velocity (v) depends upon the basal fluid or blood pressure (P), local change in fluid or blood pressure ($\Delta P$), the blood density ($\rho_b$), and local relative volume changes ($V_b/\Delta V_b$), then dimensional analysis indicates that the general functional relationship between all these quantities must have the form:

$$F\left(\frac{\rho_b v^2}{\Delta P}\right) = G\left(\frac{V_b}{\Delta V_b}, \frac{P}{\Delta P}\right) \quad \{10\}$$

with F and G indicating functions of the type shown.

The generalized functional relationship of Equation {10} and its derivatives, relate fluid density to fluid parameters like pressure, volume, and wave velocity, all of which can be measured by noninvasive means. The most difficult parameters to measure noninvasively in Equation {10} are the fluid volume ($V_b$) and change in fluid volume ($\Delta V_b$) values. Even though the inventors disclose a preferred embodiment of this invention using impedance sensing as a means of measuring these parameters, it is anticipated that any methods or means including, but not limited to, optical, ultrasound, and magnetic resonance imaging used to measure basal volume and volume changes noninvasively can be useful in practicing this invention.

The simplest relation of this type, obtained after neglecting pressure ratio effects, is $$\frac{\rho_b v^2}{\Delta P} = \frac{V_b}{\Delta V_b} \quad \{11\}$$

which is recognized as a rearrangement of the Bramwell-Hill Equation {9}. It can be seen that to solve Equation {11} or its general form Equation {10} for the fluid density one must be able to measure the fluid volume and changes in the fluid volume.

For purposes of this disclosure, an important corollary of Nyboer's work is the relationship between volume and admittance in a tubular segment:

$$\frac{V_b}{\Delta V_b} = \frac{Y_b}{\Delta Y_b} \quad \{12\}$$

where the subscript $_b$ refers to blood, Y is admittance (Y=1/Z), $Y_b$ is the initial admittance and $\Delta Y_b$ is the change in admittance associated with the change in pressure. Since V=$\rho$L/Z and $\Delta$V=$\rho$L/$\Delta$Z then it can be seen that the ratio of $\Delta$V/V reduces to 1/$\Delta$Z/1/Z which is the same as $\Delta$Y/Y. In this case $\rho$ denotes the resistivity of the blood. Since it has been shown that the resistivity of the blood varies with hematocrit in the above cited Shankar article, then it is useful to eliminate the affects of resistivity on the calculations of blood density when using impedance as a volume indicator. Using this corollary, the expression $Y_b/\Delta Y_b$ can be substituted for the volume ratio $V_b/\Delta V_b$ in Equation {11}. This substitution removes any dependence upon the unknown resistivity of the blood in the density calculation. $Y_b$ is the initial admittance of the vessel and $\Delta Y_b$ is the change in admittance due to the volume/pressure wave propagating along the vessel. Both these quantities are measured by the invention. This substitution of admittance ratio for volume ratio, and slight rearrangement, leads to an expression for the blood density.

$$\rho_b = \frac{\Delta P * Y_b}{v^2 * \Delta Y_b} \quad \{13\}$$

The velocity of the wave can be represented as the time that the wave takes to move a given distance along the vessel divided by that distance (v=L/t). L is the known distance between measuring electrodes and t is the measured time difference when the pulse wave is detected at each electrode. This relation for velocity can be substituted into the equation {13} to yield the equation for blood density as a function of noninvasively measurable quantities.

$$\rho_b = \Delta P * \frac{Y_b}{\Delta Y_b} * \frac{t^2}{L^2} \quad \{14\}$$

It can be seen that the local relative volume ratio or change ($V_b/\Delta V_b$) of Equation {10} is a fundamental parameter needed for solving Equation {10} for fluid density, and thus other methods of measuring fluid volume and fluid volume changes including but not limited to optical, tonometric, ultrasound, and magnetic resonance would be suitable for practicing this invention. Regardless of when such new relations are derived or discovered, they can be evaluated from the measurement technology of the current invention to obtain blood density. Thus the current invention does not depend specifically upon the use of the Bramwell-Hill equation or impedance sensing to measure blood density. Rather, it is applicable to all such relations of the form expressed by Equation {10} that describe pulse propagation.

Blood Density to Hematocrit

In current clinical practice the specific gravity, or density, of the whole blood is of little clinical value, since physicians and nurses are trained to relate to measured values of hematocrit, hemoglobin, or Red Blood Cell Count (RBC). Whole blood is primarily composed of two substances (plasma and red blood cells), each of which have different, but stable, densities or specific gravities. When plasma and red blood cells are combined to make whole blood, the density of the whole blood is a composite value of the densities of the component parts based upon the relative concentrations of these two primary substances.

The empirical relationship between blood density and hematocrit has been shown to be linear as hematocrit varies from 0% to 100% and blood density varies from that of plasma alone to pure red blood cells alone. Thus hematocrit can be defined in terms of densities by the relationship:

$$Hct = \frac{\rho_b - \rho_{plasma}}{\rho_{bc} - \rho_{plasma}} \quad \{15\}$$

where $\rho_b$ is the density of the blood derived above with Equation {14}. Altman reported that the density of plasma ($\rho_{plasma}$) ranged from 1.024 to 1.030 for 574 male subjects with a mean value of 1.027. Altman, Philip L., Dittmer, Dorothy S., Eds., *Blood and Other Body Fluids*, Federation of American Societies For Experimental Biology, Washington, D.C., 1961. Spector, supra., reported blood plasma specific gravity ranging from 1.022 to 1.026 with a mean of 1.024. Altman reported the red blood cell specific gravity ($\rho_{bc}$) ranging from 1.0942 to 1.1069 with a mean value of 1.0989 and Spector reported a range of 1.089 to 1.097 with a mean value of 1.093. Using the average of the mean values reported by these two sources (1.0255 for $\rho_{plasma}$ and 1.09595 for $\rho_{bc}$) results in a formula that yields hematocrit in terms of several measurable or known parameters.

$$Hct = \frac{\left(\Delta P \times \frac{Y_b}{\Delta Y_b} \times \frac{t^2}{L^2}\right) - \rho_{plasma}}{\rho_{bc} - \rho_{plasma}} \times 100 \quad \{16\}$$

In Equation {16} $\Delta P$ represents the pulse pressure that is associated with a change in volume of the vessel. In the artery it is the difference between diastolic and systolic pressure. $Y_b/\Delta Y_b$ is the ratio of the admittance of the blood in the artery before any pressure change to the change in admittance when the pressure is increased by $\Delta P$. The variable t represents the time it takes for the pressure wave to travel between the two displaced impedance channels that are a distance L apart.

Figure 5:
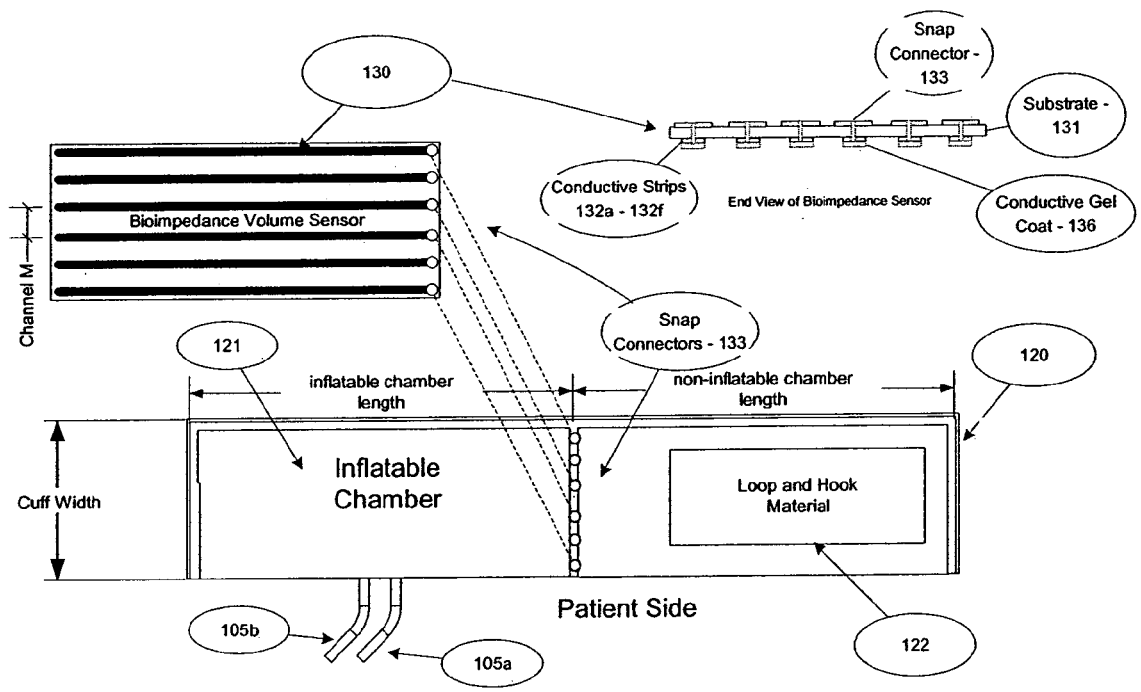
Figure 6:
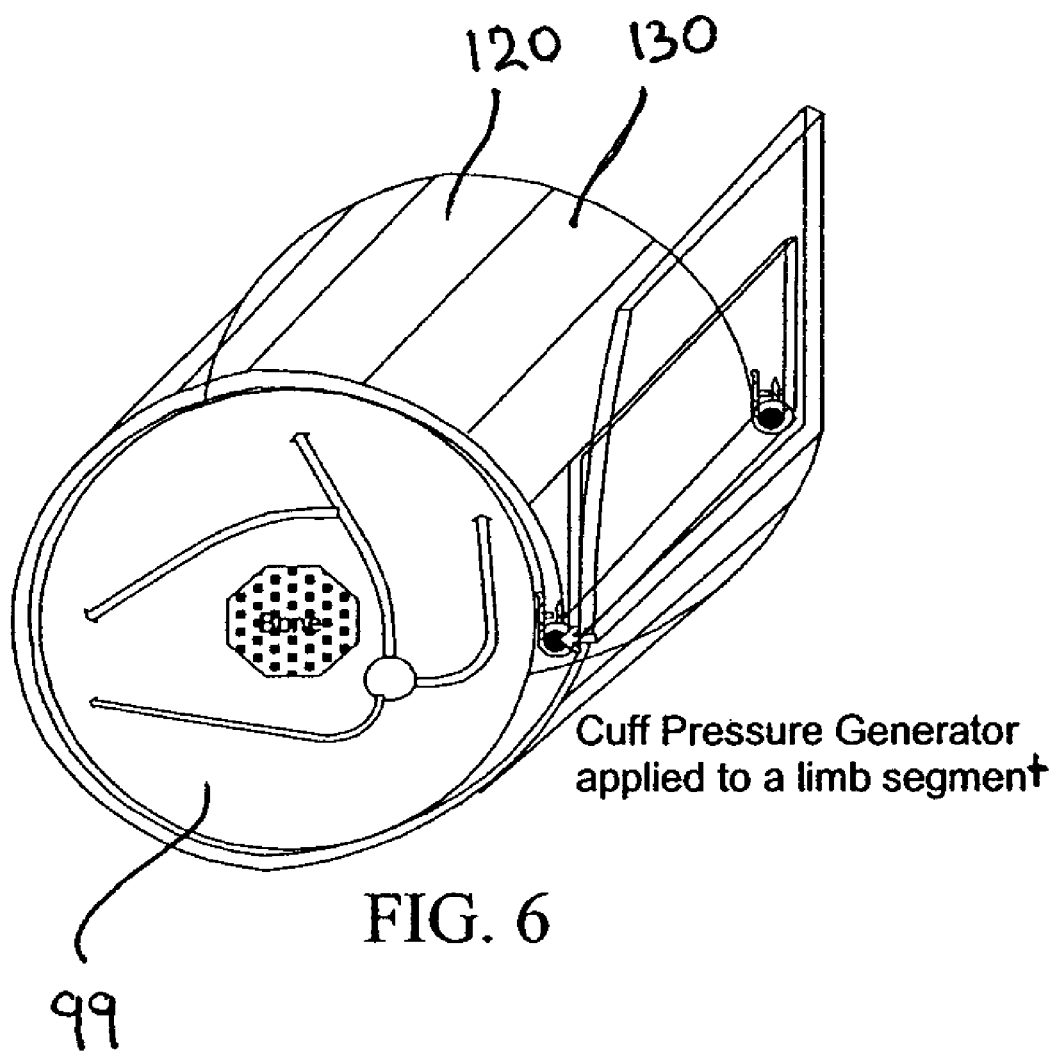
FIG. 6 is a cross sectional view of a subject's arm showing the cuff and impedance sensor applied.
Figure 7:
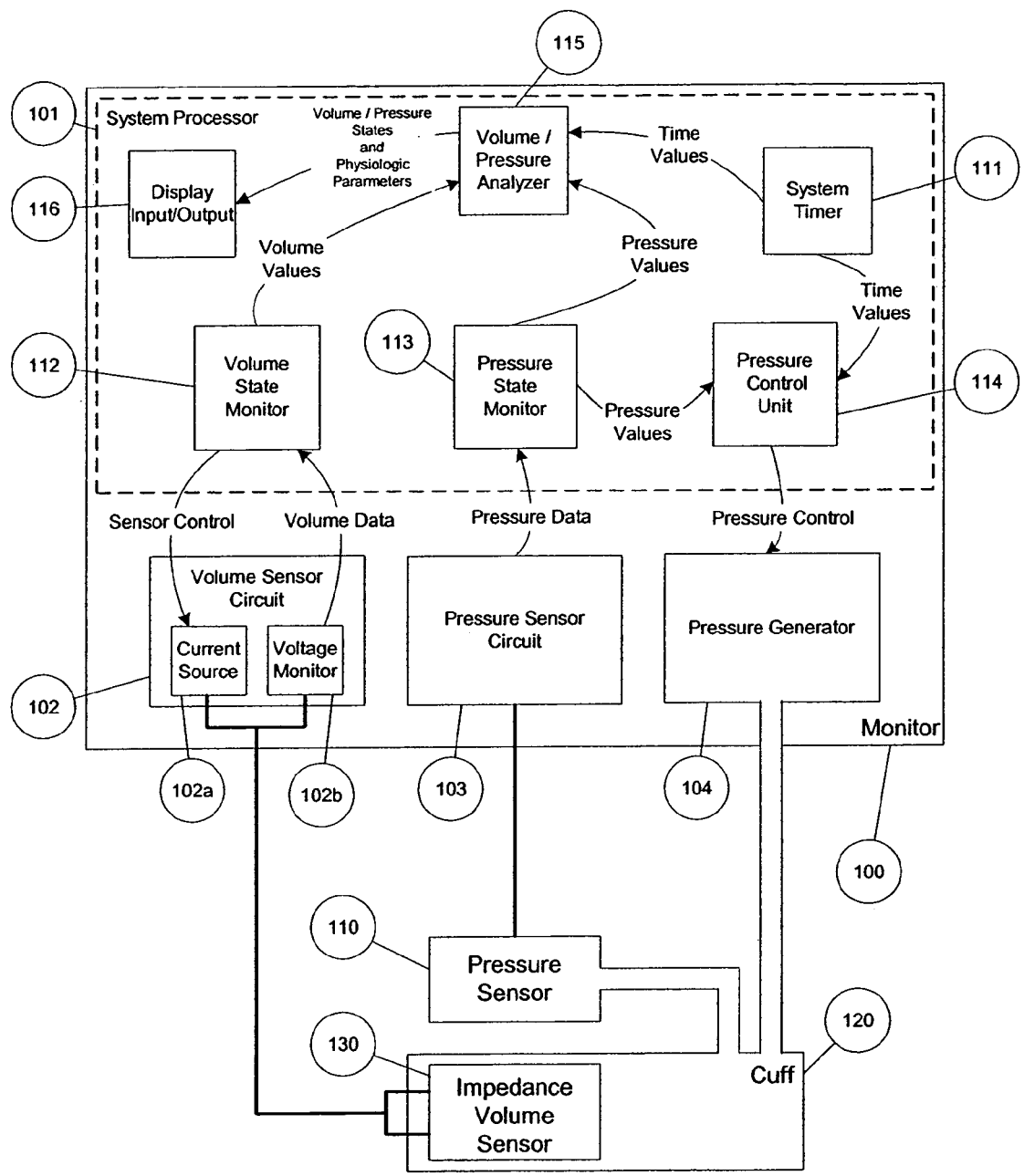
FIG. 7 is a block diagram of one embodiment of the present invention, comprising a pressure sensor, an inflatable cuff pressure generator, a bioimpedance fluid volume sensor, and a monitor.

A first exemplary embodiment of the present invention, as shown in FIGS. 4 through 13, and summarized in the block diagram of FIG. 7, comprises an impedance volume sensor 130, an inflatable cuff pressure generator 120, a pressure sensor 110, and a Monitor 100.

Impedance Volume Sensor (130)

Figure 4:
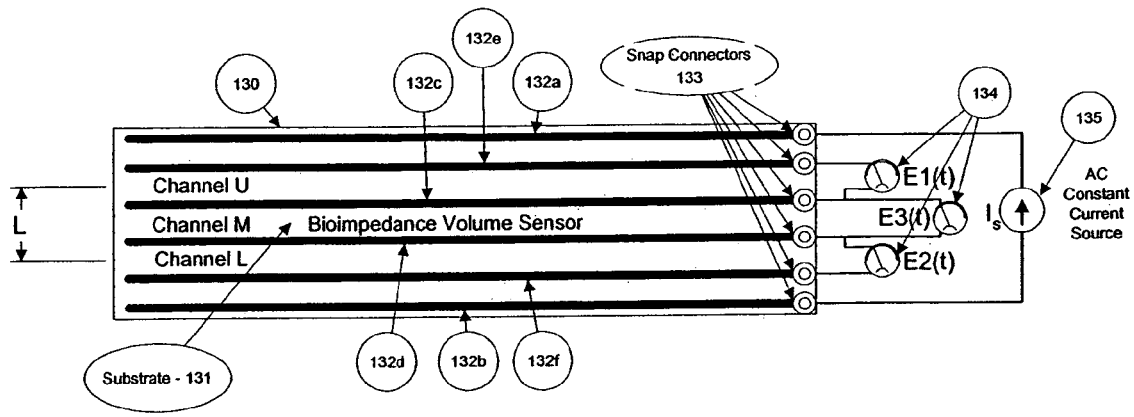
FIGS. 4 and 5 are illustrations of the impedance sensor in three planes and indicates the various measuring channels.

Referring to FIGS. 4 and 5, the impedance volume sensor 130 may be a bio-impedance sensor comprised of a matrix of four or more parallel conductive lines, here 132a–132f, fixed to a flexible substrate material 131, e.g., similar to MYLAR®, with snap connectors 133 on one end of each conductive line as shown in FIGS. 4 and 5. It is desirable that the substrate firmly maintains the separation between conductive lines, as further discussed below. The impedance volume sensor 130 is fitted to the patient side of the inflatable-cuff pressure generator 120, i.e., the side intended to be applied to the surface of the body of the subject. The alignment of pressure generator 120 and impedance volume sensor 130 is such that the volume sensor is centered under the inflatable bladder portion of the inflatable cuff pressure generator 120.

The impedance volume sensor shown in FIGS. 4 and 5 derives its measurements from conductive lines 132a–132f that may be produced with conductive paint or other material suitable for bio-impedance monitoring. Furthermore, the conductive lines may be coated with a gel material 136 suitable for reducing the high resistance layer of the skin of the subject, without causing adverse chemical reaction. Alternatively, point electrodes might be used in the impedance sensor, although signal to noise issues may result.

The excitation leads 132a and 132b are the input and output connections for the AC constant amplitude current source 135. The constant current source delivers a nominal 50 kHz, 1.2 mA RMS, constant amplitude, alternating current to the body region of the subject. It is anticipated by the inventors that the constant amplitude current is desirably an alternating current of a frequency capable of producing a uniform current density within the body region for normal operation of the invention. This constant amplitude alternating current establishes a circuit through the patient limb creating a voltage drop along the current path that is proportional to the impedance of the tissue bed. Voltage drops are measured between electrode elements that generate voltages E1, E2, and E3 134 as shown in FIG. 4.

The distance between the center conductive lines 132c and 132d of the impedance volume sensor 130 defines the width of the middle measurement channel (Channel M), and therefore defines the body region that will be used by the invention to measure blood volumes. A desirable separation of the conductive lines, which define Channel M of impedance volume sensor 130, is less than the cuff width divided by five. Furthermore, Channel M should be located in the middle of the inflatable cuff width. Impedance volume sensor 130 is preferably coextensive with but not wider than the cuff 120. The sensing leads 132c, 132d, 132e, and 132f should be positioned between the excitation leads 132a and 132b.

In FIG. 4 the upper and lower channels (Channels U and L) formed by the upper two sensing leads 132c and 132e and the lower two sensing leads 132d and 132f are used for the velocity measurement. Thus the separation between these two channels represents the length L over which the pulse wave velocity is measured. This dimension is constant for all measurements using the same geometry sensor and therefore can be treated as a calibration constant in the hematocrit calculations.

The impedance volume sensor 130 is attached to the inflatable cuff 120 by a connector system. This could, e.g., be individual snap connectors 133, or a connector bank with some latching mechanism for locking the impedance volume sensor into place and creating the electrical circuits for the impedance volume sensing.

Once the impedance volume sensor is mated with the inflatable cuff, the combination unit 120 and 130 may be applied circumferentially to a limb of the subject 99 as shown in FIG. 6. The inflatable cuff is preferably wrapped around the upper arm of the subject with the impedance volume sensor applied directly to the skin of the subject. The inflatable cuff is wrapped snugly around the limb of the subject with the conductive lines preferably running at substantially a right angle to the length of the limb. Adhesive may be used to secure the conductive lines to the subject.

Cuff Pressure Generator (120)

Pressure applicator or generator 120 is an inflatable cuff, as shown in FIG. 5, using air or other fluid for inflation of the cuff bladder or chamber 121. The cuff may be circumferentially fitted around an appendage of the subject (FIG. 6) including, but not limited to, an arm, leg, finger, or toe in such a manner as to be capable of generating pressure against the body region of the subject. The pressure generator 120 is secured to the subject in this exemplary embodiment by hook and loop material 122 which is commonly used for blood pressure cuff application.

A common blood pressure cuff, as shown in FIG. 5, is the prevalent method available for applying pressure against a body region for physiologic parameter measurement. Since it may be commercially advantageous to use commonly available blood pressure cuffs for pressure generation in certain aspects of the present invention, the inventors have observed that a reasonably accurate determination of blood admittance, or volume, versus pressure data can be accomplished if the volume measuring region defined by the width between sensor leads 132c, 132d of the bio-impedance sensor 130 (FIG. 4), is kept narrow relative to the width of the inflatable bladder 121. It is also desirable that if the volume measuring region defined by sensors 132c, 132d is located at the center of the inflatable bladder as shown in FIG. 4. Desirably, the width of this region should not exceed one fifth of the cuff width for reasonably accurate determinations of volume/pressure values.

Pressure Sensor (110)

Figure 9:
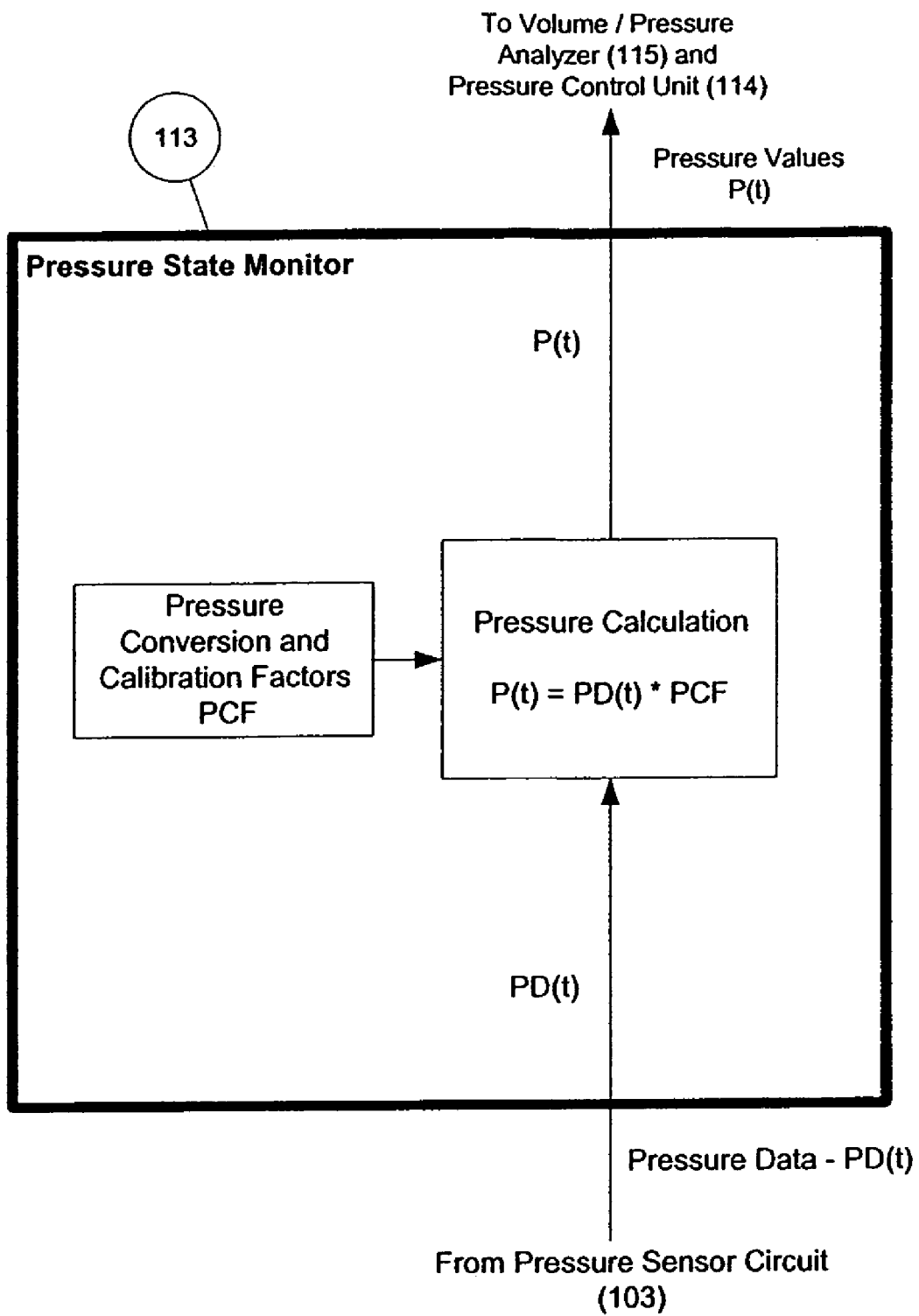
Figure 10:
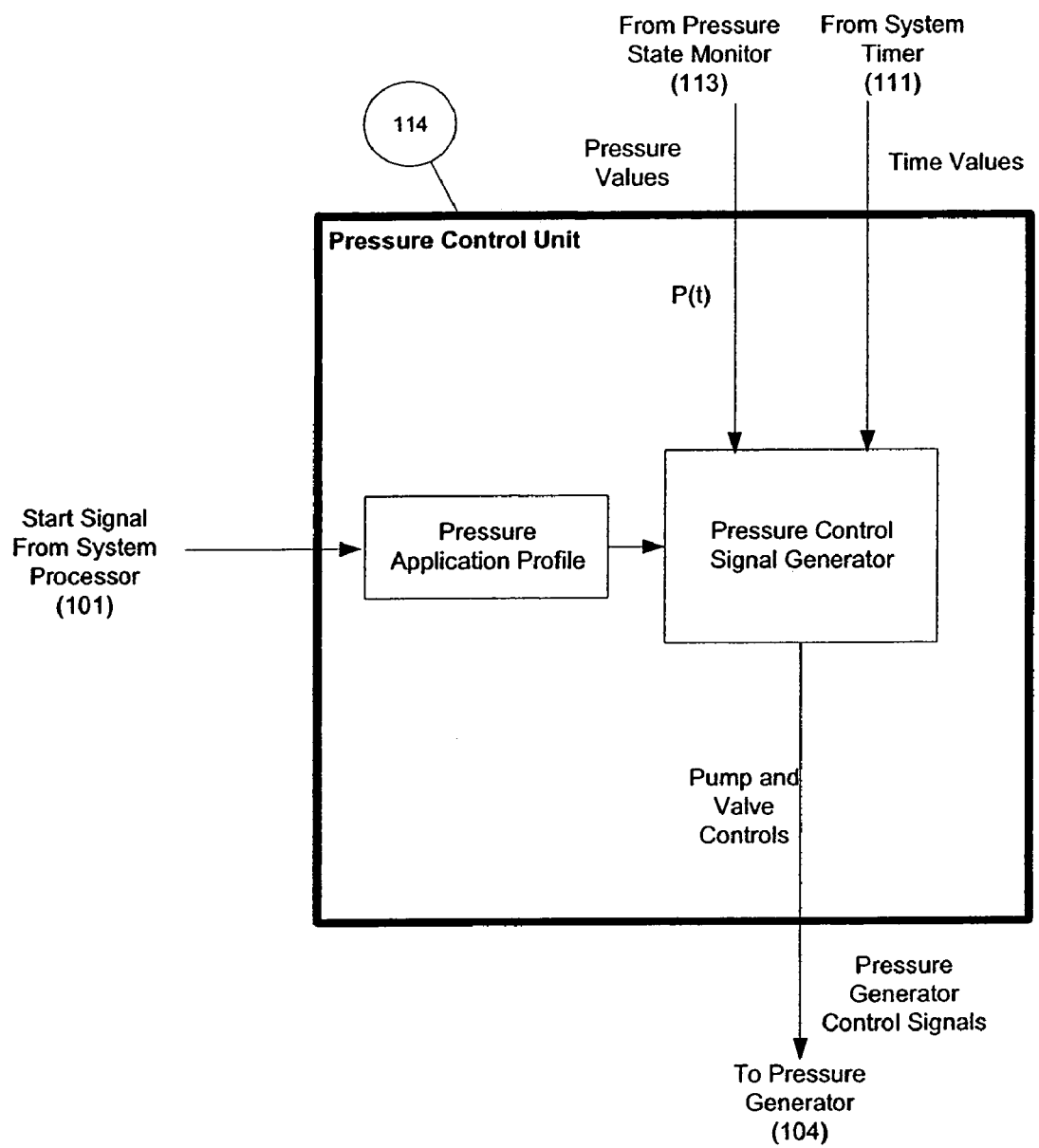

The pressure sensor 110, as shown in FIG. 7, preferably measures the pressure produced at the cuff 120, rather than at the pump for greater accuracy. The pressure sensor 110 produces an electronic signal representing pressure data. The pressure signal is received by the pressure sensor circuit 103 which produces pressure data. The pressure data is in turn received by the pressure state monitor 113 and processed into pressure values as shown in FIG. 9. The pressure values are sent to the pressure control unit 114 for feedback control and to the volume pressure analyzer 115 for analysis.

Monitor (100)

As shown in the block diagram (FIG. 7) the monitor 100 comprises four major subsections: the system processor and calculator 101, the volume sensor circuit 102, the pressure sensor circuit 103, and the pressure generator 104. In this embodiment the volume sensor circuit 102 (FIG. 11), the pressure sensor circuit 103, and the pressure generator 104 (FIG. 8) are seen to be implemented in hardware. Each of these functions could be accomplished in many different ways, and only a representative solution is presented. In this implementation the system processor 101 is implemented as a microprocessor and the various functions 111 through 116 illustrated in FIG. 7 and their necessary calculations are performed in software. They could, however, be performed by dedicated hardware.

Figure 11:
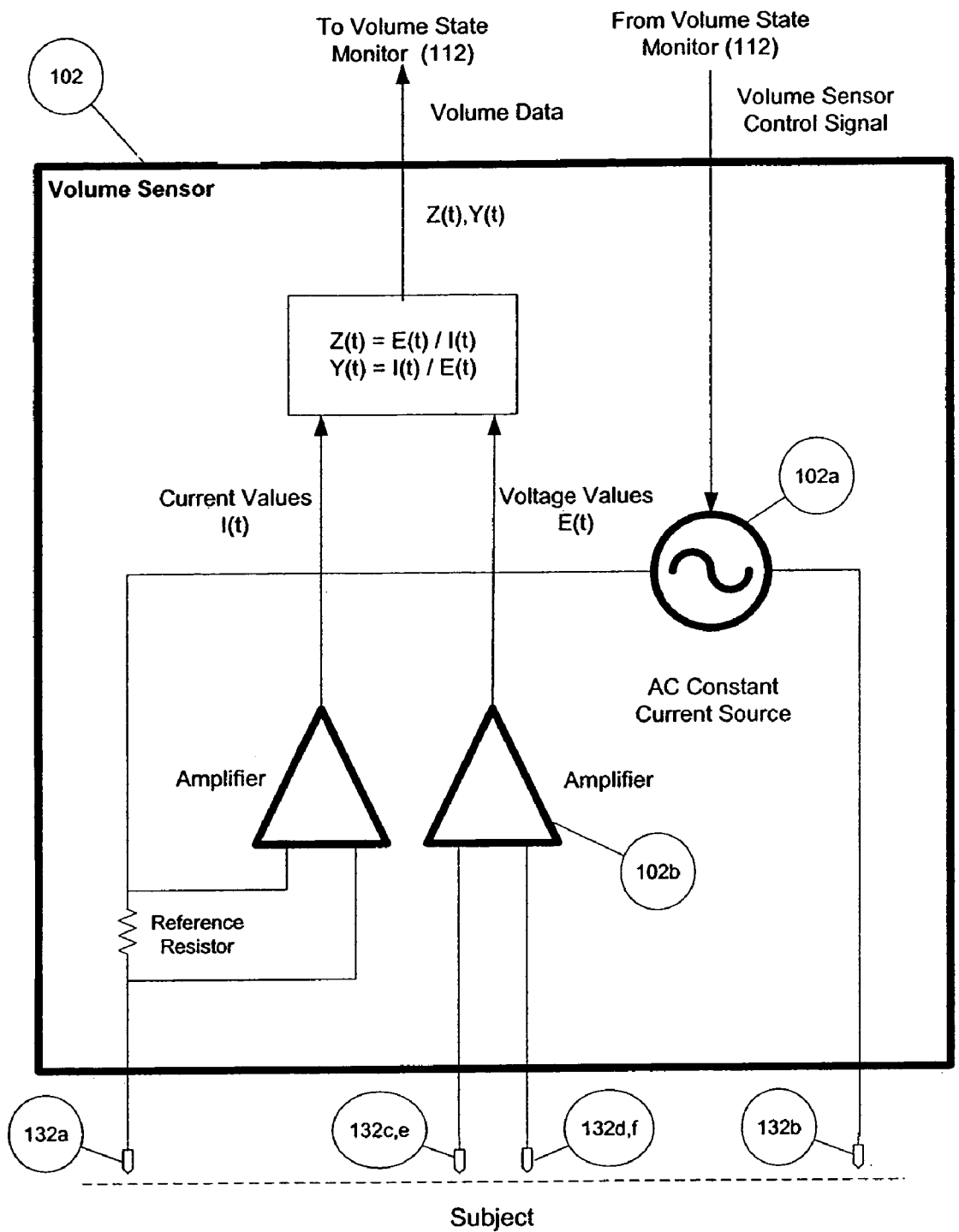
Figure 12:
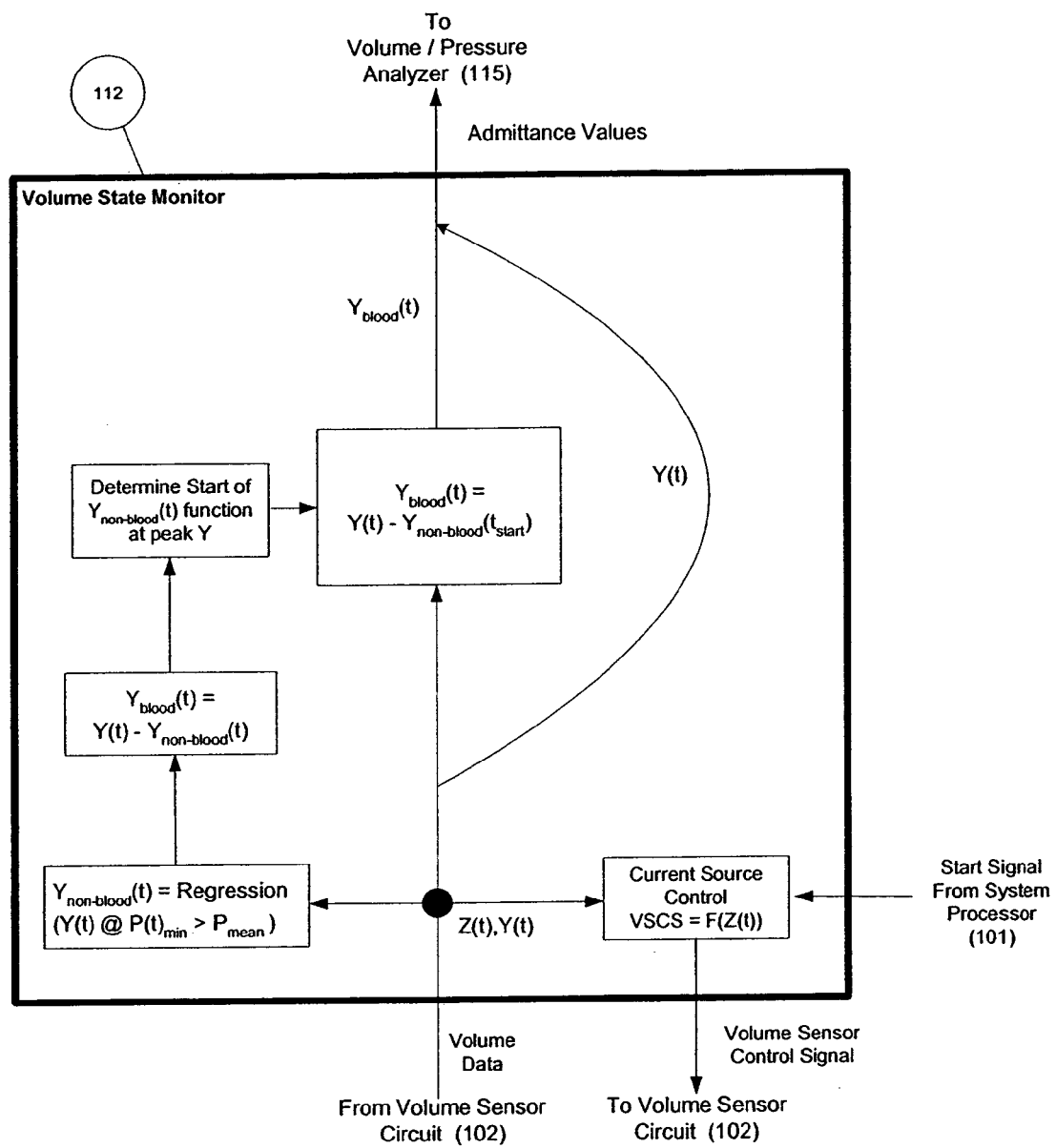

The volume sensor circuit 102, as seen in FIG. 11, consists of an AC constant current source 102a and an amplifier for each channel 102b to measure the voltage generated across the channel electrodes by the applied current from the current source 102a. The volume sensor circuit 102 produces volume data including any data indicative of volume or volume changes in the body region of the subject. Therefore, the volume sensor circuit 102 may measure absolute, calibrated, relative or proportional (admittance) volume data from the body region. In addition, there is a reference channel for correcting for any inaccuracies in the constant current source. An analog to digital conversion is then performed on the output of these amplifiers and the results combined as shown in FIG. 11 to produce admittance volume data. The admittance volume data is passed to the system processor.

The pressure sensor circuit 103 amplifies and converts the analog electrical signal output from the pressure sensor to digital data. This digital data is then passed on to the system processor 101 as pressure data. In addition the pressure sensor circuit provides whatever source or stimulation is required by the particular type of pressure sensor used.

Figure 8:
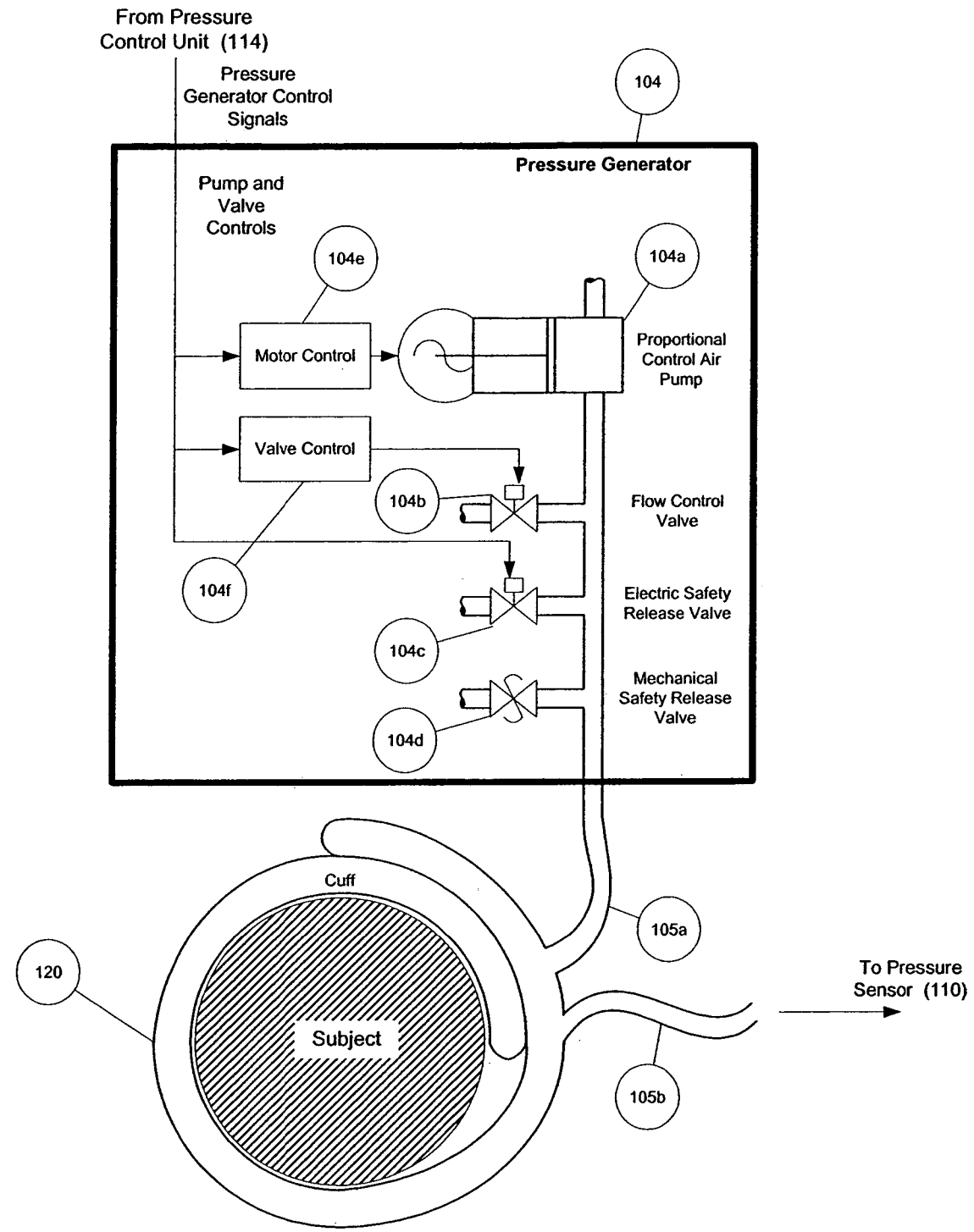
FIGS. 8 through 13 are enlargements of the various other functional blocks shown in the block diagram of FIG. 7 and depict the internal functions of these blocks.

The pressure generator 104, as seen in FIG. 8, consists of a pump 104a and several valves 104b, 104c, and 104d along with control circuitry 104e and 104f to control them. The pressure generator 104 may include any means and method for applying and relieving pressure to a body region of a subject in a controlled manner. The pressure generator 104 may be capable of applying increasing or decreasing pressure at a linear, nonlinear, or step-wise rate of change of pressure versus time. Furthermore, the pressure generator 104 can be capable of holding pressure at a pressure level for a period of time, or dithering above and below a pressure level over a period of time. While more elaborate configurations employing multiple pumps and more valves can be used to improve the linearity, accuracy, and smoothness of the pressure generation, the configuration shown in FIG. 8 is sufficient to demonstrate the basic function required. These more elaborate configurations are considered to be possible in other embodiments of the invention.

The system processor 101 shown in FIG. 7 shows several functional blocks that would be implemented in software in this embodiment. These are the system timer 111, the volume state monitor 112, the pressure state monitor 113, the pressure control unit 114, the volume/pressure analyzer 115, and the display input/output 116. These blocks represent steps in the analysis of the data from raw A-to-D converter data to finished physiologic parameters.

The system timer 111 is a highly accurate time base for all of the functions of the system processor. It provides the sample rate timing as well as timing for controlling the various functions of the monitor 100. In this embodiment of the invention the time base is derived from the system clock of the microprocessor.

The volume state monitor 112 (FIG. 12) is a computational routine that performs the conversion of raw volume data from the volume sensor circuit 102 in the form of impedances or admittances, to actual blood volumes. An array is made of this data as a function of time. In addition it performs the non-blood data subtraction routine which results in an array of the basal admittance of the blood ($Y_b$) used in the density and hematocrit calculation.

The pressure state monitor 113 (FIG. 9) is a computational routine that performs the conversion of raw pressure data to calibrated pressure.

The pressure control unit 114 (FIG. 10) is a control routine which uses the pressure values from the pressure state monitor 113 together with a programmed pressure profile to control the pressure generator 104. It operates in such a manner as to cause the pressure in the cuff to precisely track the pressure profile up or down over time.

The volume/pressure analyzer 115 (FIG. 13) performs the fundamental calculations resulting in output parameters. In the case of this embodiment, it uses the pressure and admittance values supplied by the volume state monitor 112 and the pressure state monitor 113 together with timing supplied by the system timer 111 to solve Equation {16} for the subject's blood density and hematocrit.

The display input/output 116 is the source for user input to the monitor and is the output device for the physiologic parameters which are the results of the above calculations. It is anticipated that many other parameters and system variables could be displayed on the device.

System Operation

Monitor 100 begins a measurement cycle when the system processor 101 generates a "start" signal. The pressure control unit 114 generates pump and valve signals for the pressure generator 104 (FIG. 8), activating the air pump 104a and closing the control valve 104b. The electrical and mechanical safety valves 104c and 104d are normally closed except in the case of a mechanical or electrical fault exceeding allowed limits for safe operation. Pressure generator 104 inflates the cuff 120 according to a pressure application profile in pressure control unit 114. The pressure application profile is a prescribed inflation/deflation rate and manner suitable for measuring pressure changes in the cuff by the pressure sensor 110 and volume changes by the impedance volume sensor 130.

The pressure signal from the pressure sensor 110 is amplified by the pressure sensor circuit 103 and applied to the pressure state monitor 113. The pressure state monitor 113 (see also FIG. 9) calibrates the pressure signal from the pressure sensor 110 for use by the pressure control unit 114 (see also FIG. 10) and the volume/pressure analyzer 15

Figure 13:
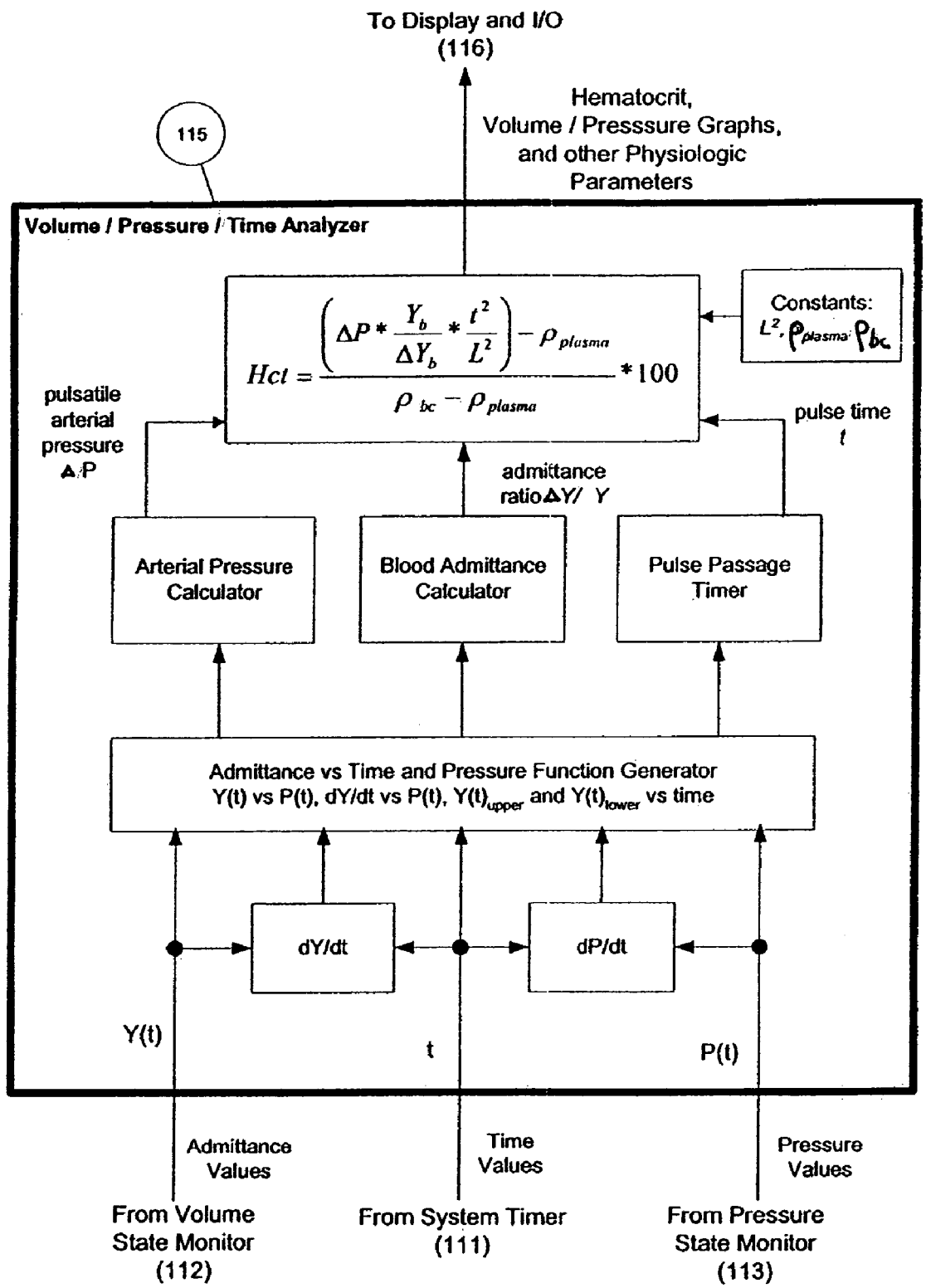

(FIG. 13). The pressure control unit 114 produces control signals for the pressure generator 104 for controlling the rate and direction of pressure change against the body. The pressure control unit 114 also controls the limits of pressure that is applied to the body region of the subject. The pressure generator 104 may apply or relieve pressure against the body region.

In response to the "start" signal from 101, the volume state monitor 112 produces volume sensor control signals for the volume sensor circuit 102. The volume sensor control signal starts the current source 102a to concurrently apply a constant current to the subject through the forcing sensor electrodes 132a and 132b on the volume sensor 130. As the pressure increases and decreases on the body segment under the volume sensor 130 due to the action of the pressure generator 104 and cuff 120, a voltage is concurrently measured between the sensing electrodes of the Upper, Middle, and Lower channels 132c, 132d, 132e, and 132f on the volume sensor 130 by the voltage monitor 102b. The volume sensor circuit 102 converts the current and voltage signals into real-time impedance (Z(t)) and admittance (Y(t)) signals.

The volume state monitor 112 receives admittance data from the volume sensor circuit 102 and processes the body segment admittance data into blood admittance values using the non-blood subtraction method described below. The volume state monitor 112 also produces volume sensor control signals for stimulating and controlling the volume sensor circuit 102. Blood volume values may be absolute, calibrated, relative, or proportional i.e. admittance to actual volumes of the subject. The volume sensor circuit 102 and volume state monitor 112 may, in combination, perform volume value determinations using any method of noninvasive detection of volume or volume changes in a body region. This includes, but is not limited to, methods of bio-impedance as illustrated, ultrasound, optical absorption, optical diffusion, optical reflection, all forms of electromagnetic energy absorption, magnetic resonance, piezoelectric, tonometric, and mechanical displacement.

As further seen in FIGS. 9–13, the volume pressure analyzer 115 acquires admittance volume values from the volume state monitor 112 while the pressure generator is increasing pressure against the body region in a linear, non-linear, or step wise manner, or while the pressure generator is holding pressure constant against the body region, or while the pressure generator is decreasing pressure against the body region in a linear, nonlinear, or step-wise manner. The volume pressure analyzer 115 receives concurrent volume values and pressure values for analysis and presentation, as illustrated by the data flow arrows. The volume pressure analyzer 115 compares the upper and lower channel real-time volume data to calculate the passage time of the pulse due to a cardiac cycle. In addition it analyzes the volume values versus pressure values of the middle channel to determine arterial pressures and calculate pulse pressure. Finally the volume pressure analyzer 115 calculates the ratio of the change in blood admittance to the blood basal admittance at the cuff pressure corresponding to the velocity measurement. These values are substituted into Equation {16} to calculate the hematocrit of the subject.

The result of this calculation is presented to the operator by the display input/output 116 as the subject's hematocrit. By this time the cuff is fully deflated and the instrument is set for the next reading.

Measurement Method

Figure 2:
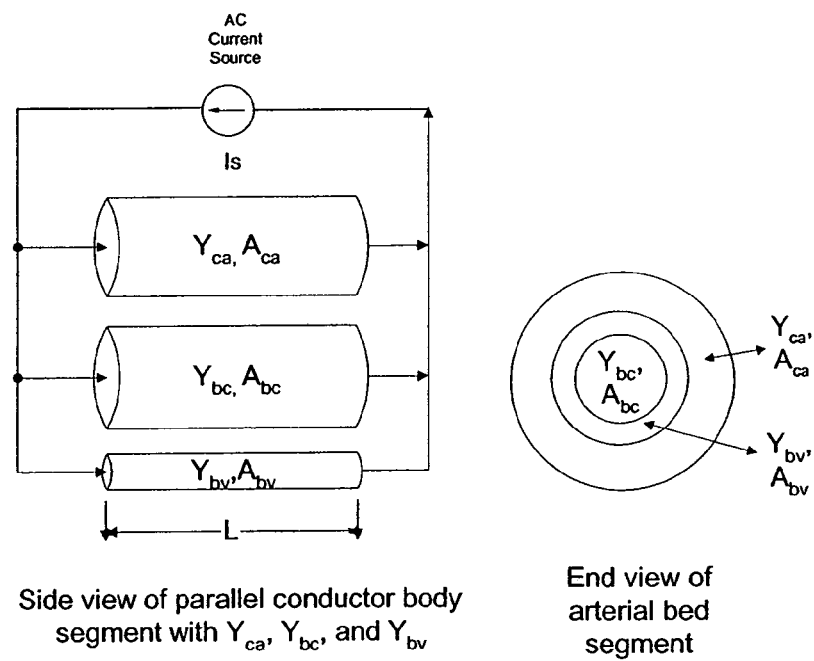
Figure 3:
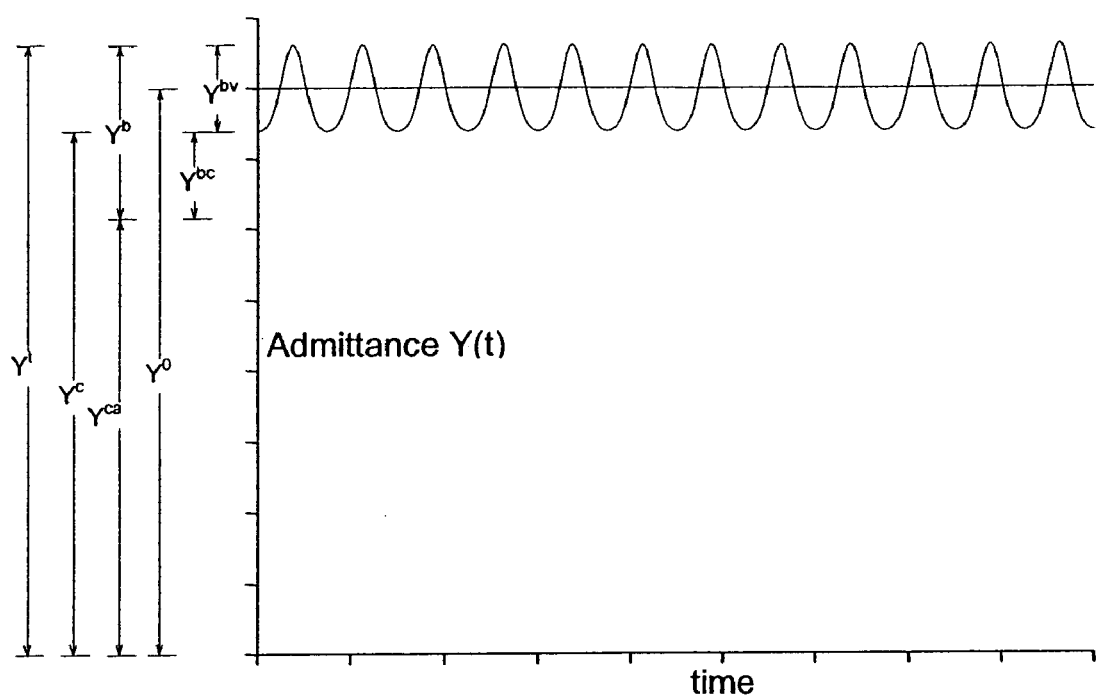
FIG. 3 is a graphical representation of the fluid admittances in a subject's limb, all of which are proportional to fluid volumes, showing how they combine to form the total volume under the pressure cuff.
Figure 14:
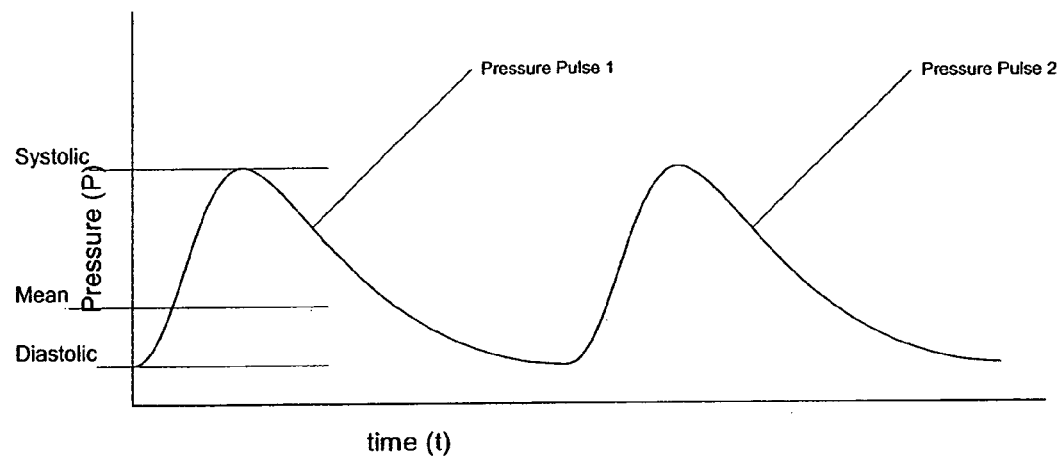
FIGS. 14 and 15 are graphs depicting the changes in pressure in the cuff over time, and indicate how various pressures are measured.
Figure 15:
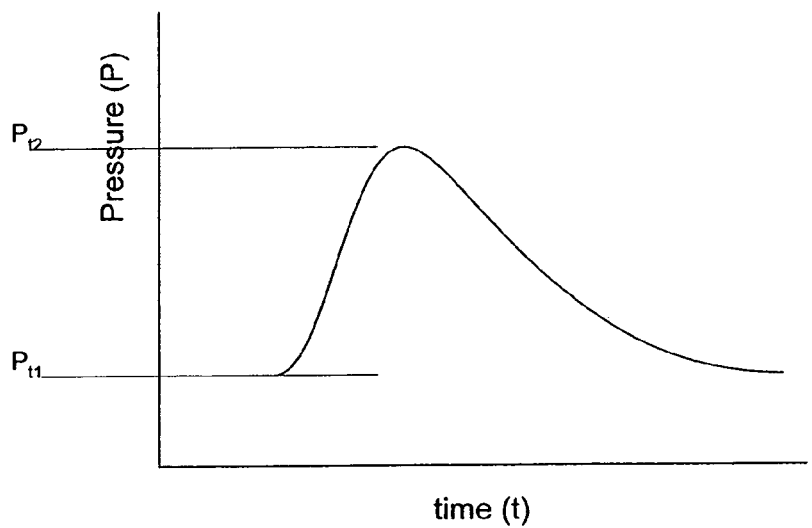

In the exemplary embodiment the voltages measured across the electrode pairs are proportional to the impedance of the tissue bed of the limb beneath the electrode pairs according to Ohm's Law (Z=E/I). The limb of a living subject is a non-homogenous material comprising lean muscle, blood, extravascular fluids, bone, and fat. The various impedance components of the limb are modeled as a parallel impedance model as shown in FIGS. 1 and 2. The impedance of a limb segment of a living subject is comprised of fixed (unchanging) parts and variable (changing) parts as can be seen in FIG. 3. For a living subject the variable part of the impedance in a limb segment is the pulsatile volume of blood that propagates through the vascular system following every heart beat (FIG. 14). The pressure pulse generated by each heart beat propagates through the vascular system at a velocity that is dependent on the volume of the vessel, the density of the blood, and the compliance of the vessel, which is defined as the change in volume generated by the pulse divided by the change in pressure. The lowest pressure that exists in the vessel at the end of each cardiac cycle is known as the Diastolic Pressure (FIGS. 14 and 15) and the highest pressure that is reached within the vessel is known as Systolic Pressure. The difference in these two pressures represents the pulse pressure propagating through the arteries. $\Delta P = P_{systolic} - P_{diastolic}$. When relationships such as Equation {9}, derived from the more general form Equation {10} are rearranged, it can be seen that the blood density, $\rho_b$, can be determined when the volume of the segment, the velocity of the pulse and the compliance of the vascular bed are known. In practice it can be difficult to determine the volumes of the vascular bed noninvasively. By using admittance as the sensing means, Equation {10} can be reduced to Equation {13}, and the volume parameters are replaced by a ratio of admittance values at the different pressure levels that define $\Delta P$. This reduction of terms makes the method achievable and practical.

Thus when the invention measures arterial pressures, pulse transit times, pulsatile changes in blood admittance, and absolute blood admittance, all of the knowledge to calculate hematocrit is present. Following is a description of the method for obtaining each of the values.

Arterial Pressures

The arterial pulse pressure is obtained by determining the systolic pressure and the diastolic pressure. There are many well-known methods for determining arterial pressures noninvasively using a pneumatic cuff such as described above. The current embodiment of the invention uses the oscillometric method for blood pressure determination, but other techniques are possible.

Pulse Transit Time

Figure 16:
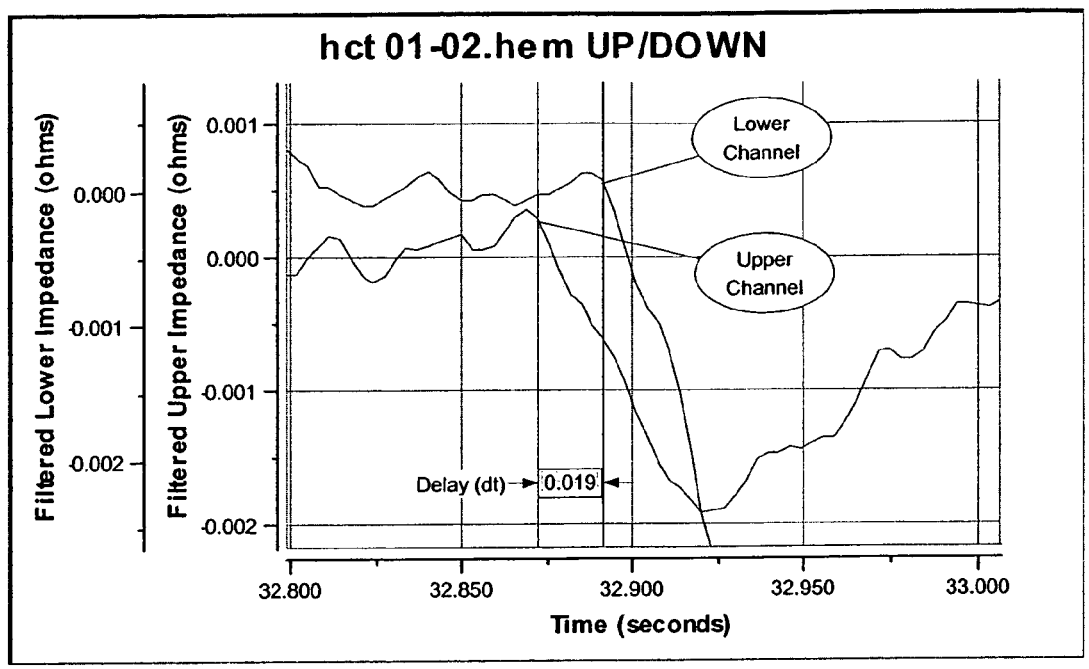
FIG. 16 is a graph depicting the change in impedance over time in each of two channels of the sensor, and indicate how the time difference between the channels is measured.

The pulse transit time is measured between the electrode pair of the Upper Channel 132c and 132e and the electrode pair of the Lower Channel 132d and 132f (FIG. 4), both of which are positioned under the sensor cuff. A variety of features of the wave-induced, time-varying admittance signal measured by these electrode pairs can be used to determine pulse transit time. These features include, but are not limited to, the peak of the wave, its foot, or the correlation time delay between a series of waves. In the embodiment of FIG. 16, the time that the pulse passed under a particular electrode pair is measured at the point where the impedance signal first starts to fall as a result of the pulse pressure wave front. In the literature, e.g., Milnor, W. R., *Hemodynamics*, $2^{nd}$ Edition, Williams & Wilkins, Baltimore, Md., 1989; and Nichols, W. W., O'Rourke, M. F., *McDonald's Blood Flow in Arteries,* 4th Edition, Oxford University Press, New York, N.Y., 1998; this is referred to as the "foot" of the pulse wave. The elapsed time between when the foot of the pulse wave passes the upper and lower electrodes is used together with the distance between the electrodes to calculate pulse wave velocity. This measurement is accomplished by holding the pressure in the cuff constant just below mean arterial pressure, and recording a series of consecutive pulses.

The data obtained from these samples is high pass filtered at about 2 Hz in order to normalize the data and to accentuate the sudden change in amplitude associated with the foot of the pressure wave as illustrated in FIG. 16.

An important benefit of applying pressure to the limb segment while making the velocity measurement is that the application dramatically slows the velocity of the pulse. This phenomena results from the fact that as pressure is increased outside the arteries in the area under the cuff, the pressure across the walls of the vessel is decreased. This unloading of the arterial walls leads to an increase in the compliance of the artery and thus an increase in the apparent compressibility of the blood. This results in a slowing of the propagating pressure wave as it passes through the region under the cuff. This slowing of the pressure wave makes the velocity measurement much easier and more accurate, but requires that the other measurements used in the calculation be made at the same cuff pressure.

Pulsatile Change in Blood Admittance

The pulsatile change in admittance corresponding to cardiac cycles, $\Delta Y$, in the body region being measured, is relatively easy to measure directly from the data. As noted by Nyboer in *Electrical Impedance Plethysmography*; this changing admittance of the region results solely from the change in volume of blood in the underlying vasculature due to a heart beat. Since the ratio of $Y/\Delta Y$ is used in the calculation of hematocrit, the value of $\Delta Y$ is measured at the same moment, i.e., same external pressure, that the value of Y is measured, as discussed below. In order to use the method of removing non-blood admittance this measurement is made as the cuff pressure is increased linearly from 0 to 180 mmHg. (see FIG. 21). The cuff pressure for the determination of $\Delta Y$ and Y is chosen to be the same as the pressure at which the pulse velocity is measured and to be just below mean pressure.

Absolute Admittance

The challenge of determining the absolute blood admittance, Y, of the region under test, at various pressures, is the ability to subtract the nonvascular admittances from the total admittance measured by the volume sensor. There are two key observations made by the inventors that allow the nonvascular admittances to be independently determined. These observations derive from the change in measured admittance of a limb segment as the applied pressure increases.

Figure 17:
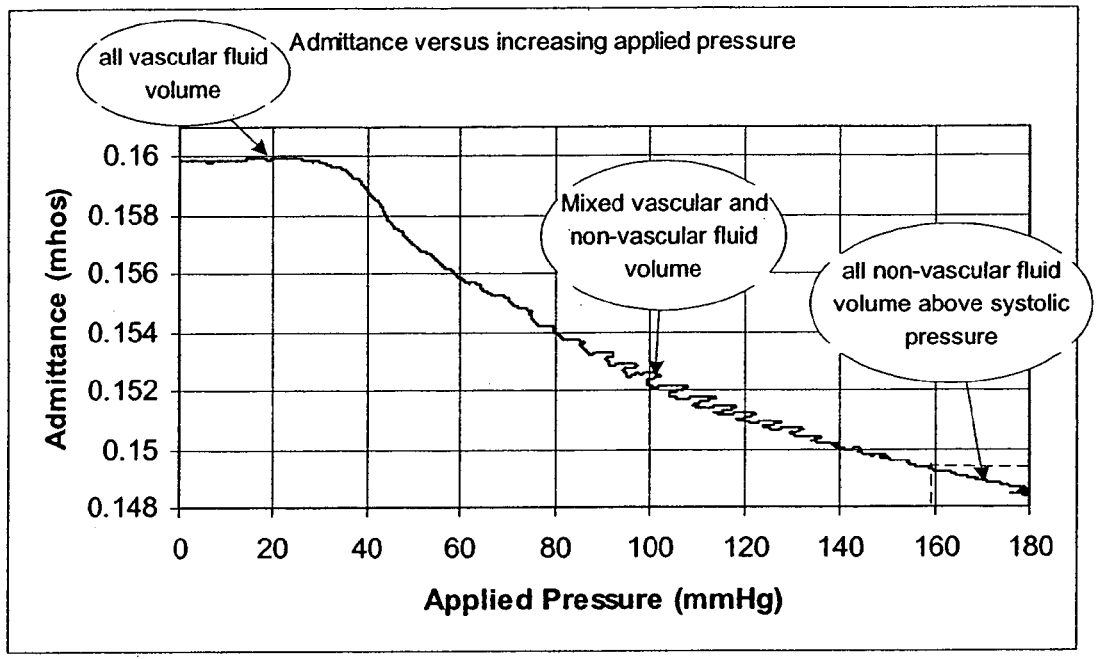
FIGS. 17 through 20 are graphs of values acquired using the apparatus shown in FIG. 7, and illustrate a methodology for subtracting non-blood admittances, leaving only the basal admittance of the blood in the artery.

The first observation, shown in FIG. 17, is that the measured total admittance continues to decrease at applied pressures higher than the highest vascular pressure ($P_{systolic}$). Since all blood is evacuated from the region when external pressures are above systolic, any changing admittance must be due to compression of the nonvascular components of the limb segment, both fluid and tissue.

The second observation is that nonvascular admittance behavior at applied pressures below systolic can be identified from the fact that the segment blood volume (admittance) goes to zero during some portion of each cardiac cycle as long as the applied pressure is greater than the mean pressure in the large arteries. Thus during some portion of each cardiac cycle at these applied pressures, all the blood has been squeezed out of the limb segment, and the remaining admittance is nonvascular. This nonvascular behavior is seen as the "floor" of the curve in FIG. 18, below systolic pressure. The short segments connecting the loops represent measured admittance values when the blood has been squeezed out of the limb segment during the portion of the cardiac cycle when the blood pressure is below the applied pressure.

The first observation delineates nonvascular admittances at applied pressures above systolic pressure, and the second gives their measured character at applied pressures down to mean blood pressure. A regression analysis links these two sets of measurements, and gives a global curve describing nonvascular admittance behavior over the entire applied pressure range. This curve can then be used to subtract nonvascular admittances from the total admittances, leaving only the blood admittances, both basal and changing. This regression and subtraction method constitutes the non-blood subtraction algorithm used to determine the blood admittance ratio, $Y_b/\Delta Y_b$, that appears in the density calculation Equation {16}.

Figure 18:
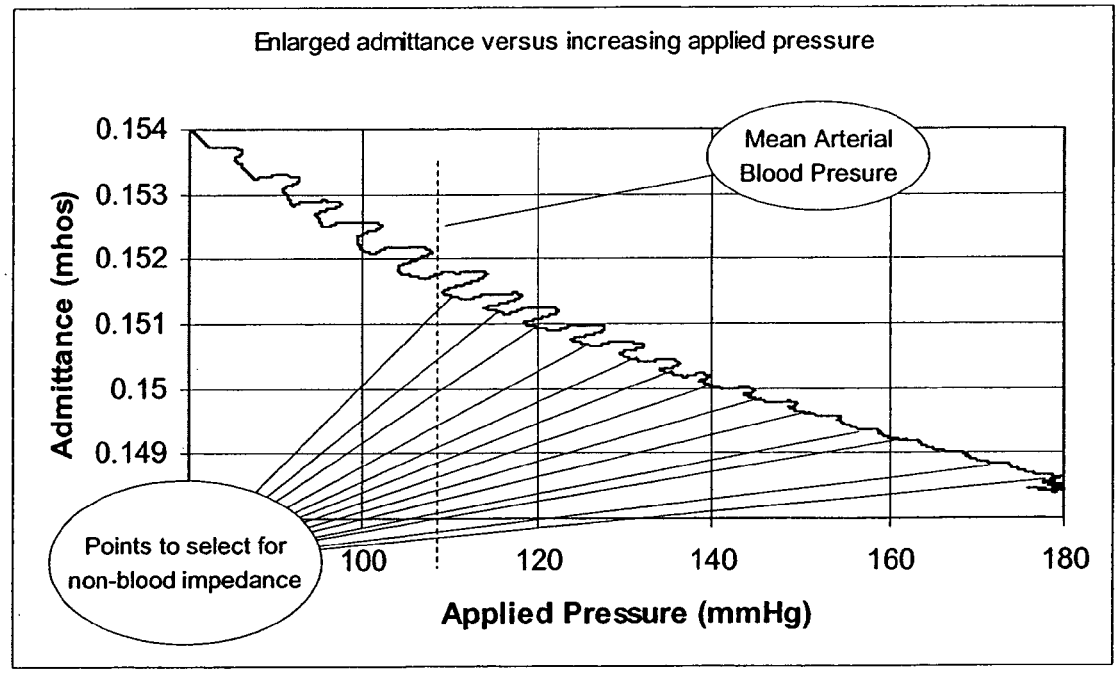
Figure 19:
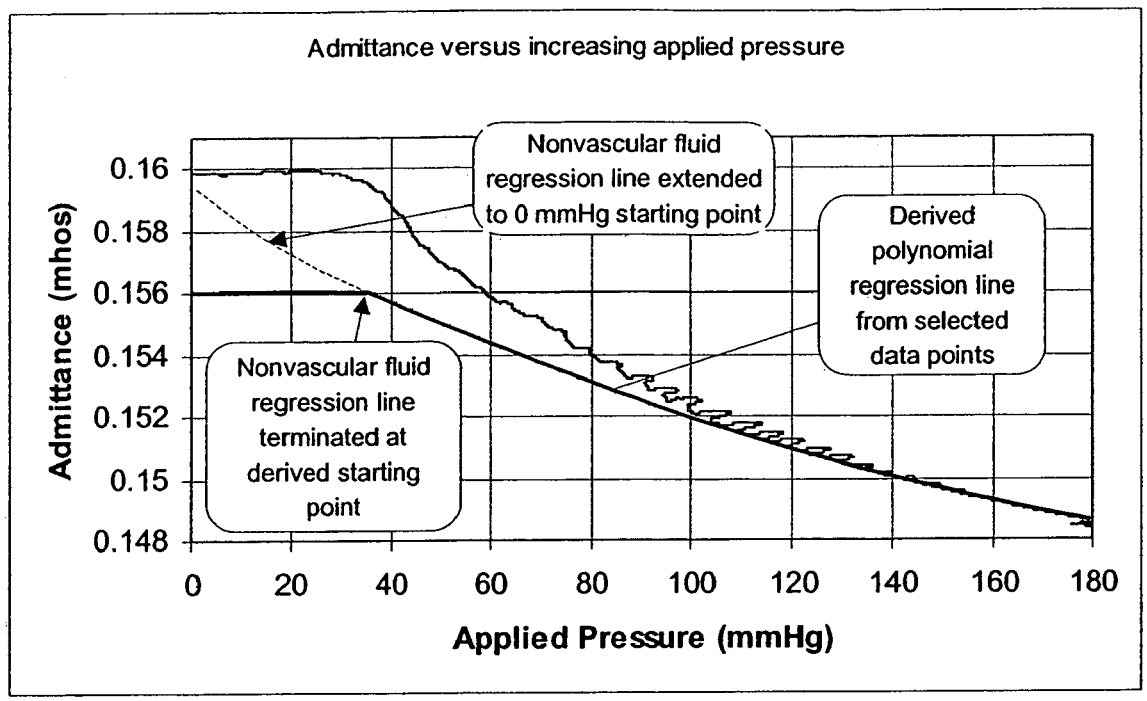
Figure 20:
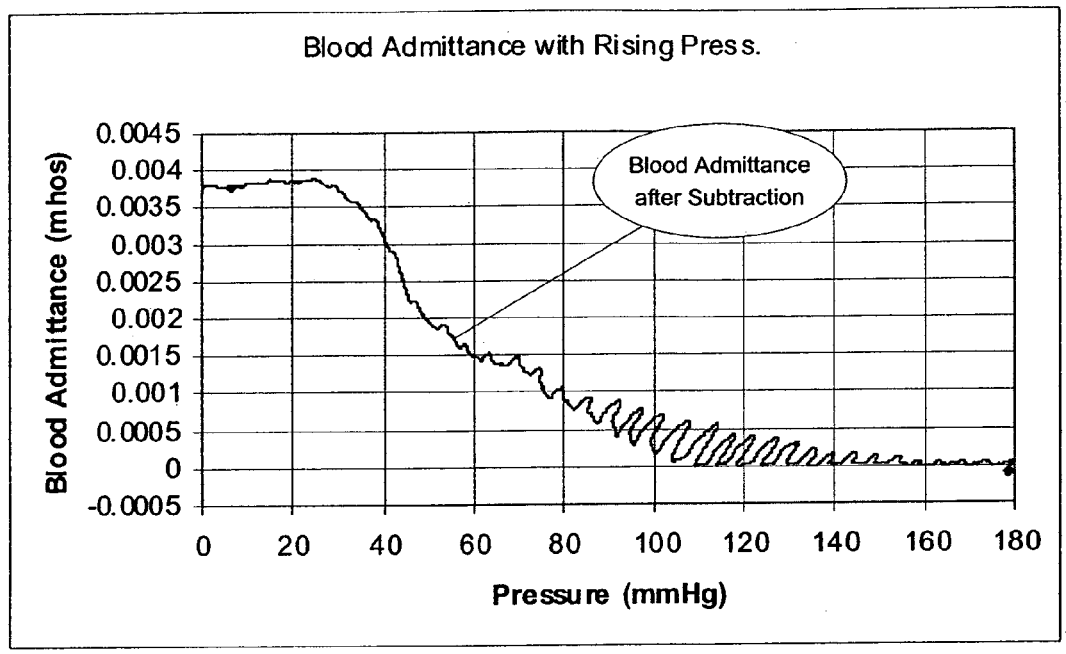

The process of determining the nonvascular admittances by regression, as illustrated in FIGS. 17, 18, and 19, allows them to be removed by subtraction from the raw data, leaving only vascular fluid related data left for further analysis, as seen in FIG. 20. This methodology is an important improvement to the art. Previously the physiologic parameters associated with the vascular fluid, such as pressure and volume, were not directly discernable from the raw data, since it could not be determined what portion of the raw data was attributable to the vascular fluid and what portion was attributable to the nonvascular components. This method makes that distinction possible.

The series of data processing steps are illustrated in FIGS. 17 through 20, which show one method of isolating the admittance values contributed by both vascular and nonvascular components in a limb segment over a wide pressure range. A fully processed Blood Volume versus Applied Pressure data set is illustrated in FIG. 20.

Pulsatile Change in Admittance to Absolute Admittance Ratio

Measuring the absolute value of admittance of the blood in a pulsatile vessel of the subject requires the use of the non-blood subtraction algorithm mentioned above. The result of applying this algorithm to a recorded measurement is shown in FIG. 21.

Figure 21:
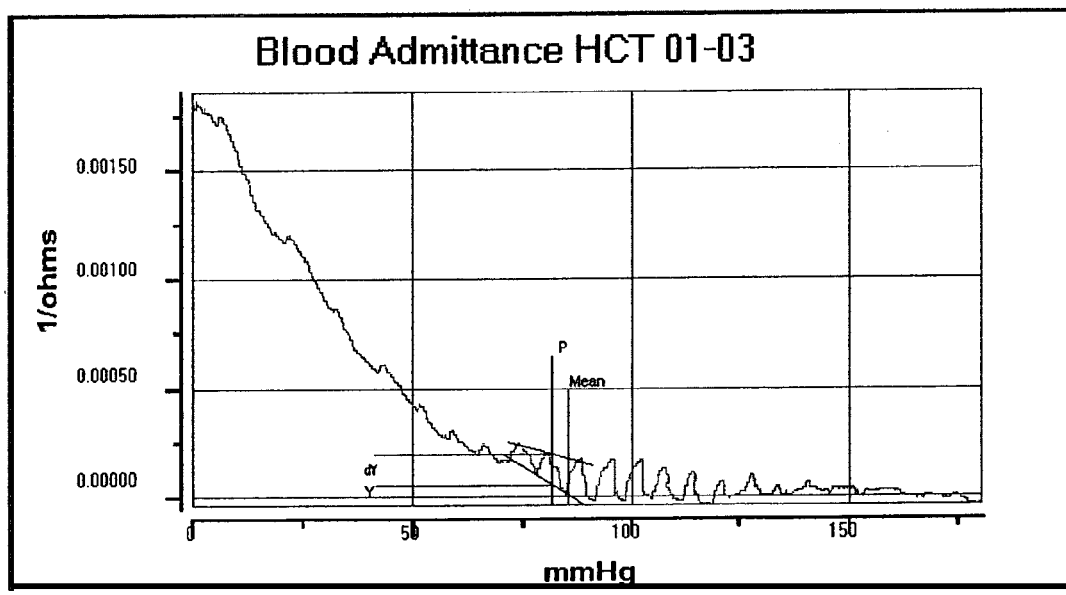
FIG. 21 is a graph depicting the admittance against cuff pressure and indicating how the ratio of the pulsatile change in admittance and the absolute value of admittance are calculated.

The graph in FIG. 21 represents the admittance (1/ohms) of the blood in the brachial artery with non-blood admittances subtracted plotted against the cuff pressure as the pressure is increased linearly from 0 to 180 mmHg. This admittance is proportional to the volume of the blood remaining in the vessels of the body region under the cuff. It can be seen that at mean pressure the basal blood admittance (proportional to blood volume) just reaches 0 when pulse pressure is at diastolic or minimum value. At pressures below mean the ratio of basal admittance at diastolic pressure and the change in admittance due to the pulse pressure can be measured. It will be noted that this value is different at different cuff pressures, but as long as it is measured at the same cuff pressure as the velocity was measured and at a pressure value less than mean the relationships described above hold. For purposes of calculating hematocrit this ratio is calculated at the pressure at which the pulse velocity was measured above.

As can be seen in FIG. 21, an interpolation is made to calculate this ratio independent of the timing of the cardiac cycle.

Hematocrit Calculation

Using the equipment and procedure described above, arterial pulse pressure ($\Delta P$), pulse transit time (t), pulsatile change in admittance ($\Delta Y$), and absolute admittance (y) are recorded from some artery of the living subject. These are then substituted into Equation {16} together with the constants of electrode separation (L), density of pure red blood cells ($\rho_{bc}$), and density of plasma ($\rho_{plasma}$) to determine the hematocrit.

It is anticipated by the inventors that the invention may be produced in multiple forms utilizing various methods of pressure generation, pressure sensing, volume sensing, mathematical operations, interface means, now known, or later developed for determination of blood density and hematocrit by the techniques set forth herein. Therefore, embodiments of the invention were provided for various forms of the invention without intent to limit the scope of the invention to any particular form or structure.

We claim:

1. A method of noninvasively measuring fluid density of a pulsed flow system with non-rigid vessel walls, comprising:
   a) noninvasively measuring a local relative fluid volume ratio $V_b/\Delta V_b$ where $V_b$ is a basal volume of fluid in a vessel and $\Delta V_b$ is a volume change of the fluid in the vessel due to the pulse;
   b) noninvasively measuring a fluid pulse propagation velocity v;
   c) noninvasively measuring a basal fluid pressure P and a local change in fluid pressure $\Delta P$;
   d) calculating fluid density $\rho_b$ as a function of the local relative fluid volume ratio, the fluid pulse propagation velocity, the basal fluid pressure, and local change in fluid pressure according to the generalized functional relationship $$F\left(\frac{\rho_b v^2}{\Delta P}\right) = G\left(\frac{V_b}{\Delta V_b}, \frac{P}{\Delta P}\right)$$

or its derivatives.

2. The method of noninvasively measuring fluid density of claim 1 wherein the fluid is blood.

3. The method of noninvasively measuring fluid density according to claim 2, further comprising deriving a hematocrit value from the blood density.

4. The method of noninvasively deriving a hematocrit value from blood density of claim 3 further comprising calculating the equation $$Hct = \frac{\rho_b - \rho_{plasma}}{\rho_{bc} - \rho_{plasma}} \times 100$$

or its derivatives;

where $\rho_b$ can be equal to $$\left(\Delta P \times \frac{Y_b}{\Delta Y_b} \times \frac{t^2}{L^2}\right)$$

where Hct is the hematocrit value, $\Delta P$ is the difference between diastolic and systolic pressure, $Y_b/\Delta Y_b$ is the ratio of the admittance of the blood in the artery before any pressure change to the change in admittance when the pressure is increased by $\Delta P$, t is the time it takes for a pressure wave to travel between the two displaced impedance channels that are a distance L apart, $\rho_b$ is the density of the blood, $\rho_{plasma}$ is the density of plasma, and $\rho_{bc}$ is the red blood cell density.

5. The method of noninvasively deriving a hematocrit value from blood density of claim 4 further comprising using an average of mean reported values for $\rho_{plasma}$ and $\rho_{bc}$.

6. The method of noninvasively measuring fluid density according to claim 1, further comprising:
   a) placing a coextensive pressure applicator and electrical impedance monitoring apparatus on a measurement area of a body;
   b) applying a constant amplitude current to the measurement area;
   c) applying pressure to the measurement area to remove blood therefrom;
   d) measuring a change in impedance values of the measurement area while applying pressure;
   e) measuring an arterial pulse pressure of the measurement area;
   f) measuring a velocity of a pulse wave of the measurement area; and
   g) deriving a blood density value from measurements of arterial pulse pressure, impedance, and velocity of pulse wave.

7. An apparatus for noninvasively measuring fluid density of a pulsed flow system with non-rigid vessel walls at a local measurement area, comprising:
   a) means for noninvasively measuring a local relative fluid volume ratio $V_b/\Delta V_b$, where $V_b$ is a basal volume of fluid in a vessel and $\Delta V_b$ is a volume change of the fluid in the vessel due to the pulse;
   b) means for noninvasively measuring a fluid pulse propagation velocity v;
   c) means for noninvasively measuring a basal fluid pressure P and a local change in fluid pressure $\Delta P$; and
   d) a calculator for determining fluid density $\rho_b$ as a function of the local relative fluid volume ratio, the fluid pulse propagation velocity, the basal fluid pressure, and local change in fluid pressure according to the generalized functional relationship $$F\left(\frac{\rho_b v^2}{\Delta P}\right) = G\left(\frac{V_b}{\Delta V_b}, \frac{P}{\Delta P}\right)$$

or its derivatives.

8. The apparatus for noninvasively measuring fluid density of claim 7 wherein the fluid is blood.

9. The apparatus for noninvasively measuring fluid density according to claim 8, further comprising means for deriving a hematocrit value from the blood density.

10. The apparatus for noninvasively deriving a hematocrit value from blood density of claim 9 further comprising means for calculating the equation $$Hct = \frac{\rho_b - \rho_{plasma}}{\rho_{bc} - \rho_{plasma}} \times 100$$

or its derivatives;
where $\rho_b$ can be equal to $$\left(\Delta P \times \frac{Y_b}{\Delta Y_b} \times \frac{t^2}{L^2}\right)$$

where Hct is the hematocrit value,
$\Delta P$ is the difference between diastolic and systolic pressure,
$Y_b/\Delta Y_b$ is the ratio of the admittance of the blood in the artery before any pressure change to the change in admittance when the pressure is increased by $\Delta P$,
t is the time it takes for a pressure wave to travel between the two displaced impedance channels that are a distance L apart,
$\rho_b$ is the density of the blood,
$\rho_{plasma}$ is the density of plasma, and
$\rho_{bc}$ is the red blood cell density.

11. The apparatus for noninvasively measuring fluid density according to claim 7, wherein the means for noninvasively measuring a local relative fluid volume ratio, means for noninvasively measuring a fluid pulse propagation velocity, and means for noninvasively measuring a basal fluid pressure and a local change in fluid pressure, further comprise:
a) a coextensive pressure applicator and electrical impedance monitoring apparatus;
b) means for applying a constant amplitude current to the measurement area; and
c) means for measuring a change in impedance values of the measurement area while applying pressure.

12. The apparatus for noninvasively measuring fluid density according to claim 7, wherein the means for noninvasively measuring a local relative fluid volume ratio, means for noninvasively measuring a fluid pulse propagation velocity, and means for noninvasively measuring a basal fluid pressure and a local change in fluid pressure, further comprise:
a) an impedance volume sensor;
b) an inflatable cuff pressure generator;
c) a pressure sensor, and
d) a monitor for determining volume states and pressure states and for controlling the application of pressure to the measurement area.

13. An apparatus for noninvasively measuring fluid density of a pulsed flow system with non-rigid vessel walls at a local measurement area, comprising:

a) a pressure applicator for applying external pressure to the local measurement area,
b) an impedance measurer coextensive with the pressure applicator; and
c) a calculator operably connected to the pressure applicator and the impedance measurer for calculating a fluid density value of the local measurement area.

14. The apparatus for noninvasively measuring fluid density of claim 13 wherein the fluid is blood.

15. The apparatus for noninvasively measuring blood density according to claim 14, further comprising a calculator for calculating a hematocrit value from the blood density value.

16. A method of noninvasively measuring fluid density of a pulsed flow system with non-rigid vessel walls, comprising:
a) noninvasively measuring a local relative fluid volume ratio $V_b/\Delta V_b$, where $V_b$ is a basal volume of fluid in a vessel and $\Delta V_b$ is a volume change of the fluid in the vessel due to the pulse;
b) noninvasively measuring a fluid pulse propagation velocity v;
c) noninvasively measuring a local change in fluid pressure $\Delta P$;
d) calculating fluid density $\rho_b$ as a function of the local relative fluid volume ratio, the fluid pulse propagation velocity, and local change in fluid pressure according to the relationship $$\frac{\rho_b v^2}{\Delta P} = \frac{V_b}{\Delta V_b}$$

or its derivatives.

17. The method of noninvasively measuring fluid density of a pulsed flow system with non-rigid vessel walls of claim 16 wherein the local relative fluid volume ratio $V_b/\Delta V_b$ is determined by:
a) measuring the electrical admittance ($Y_b$) of the basal fluid volume;
b) measuring the electrical admittance change ($\Delta Y_b$) due to increased local volume from pulsed flow; and
c) equating $$\frac{Y_b}{\Delta Y_b} = \frac{V_b}{\Delta V_b},$$

whereby the need to know the resistivity of the fluid in determining the local fluid volume ratio is eliminated.

18. A method of noninvasively measuring a local relative fluid volume ratio $V_b/\Delta V_b$ in a pulsed flow system with non-rigid vessel walls comprising:
a) measuring the electrical admittance ($Y_b$) of the local basal fluid volume;
b) measuring the electrical admittance change ($\Delta Y_b$) due to increased local volume from pulsed flow; and
c) equating $$\frac{Y_b}{\Delta Y_b} = \frac{V_b}{\Delta V_b},$$

whereby the need to know the resistivity of the fluid in determining the local fluid volume ratio is eliminated.

19. A method of determining a hematocrit value of blood comprising:
   a) measuring density of the blood ($\rho_b$); and
   b) determining the hematocrit value according to the relationship $$Hct = \frac{\rho_b - \rho_{plasma}}{\rho_{bc} - \rho_{plasma}} \times 100,$$

wherein $\rho_{bc}$ is the red blood cell density and $\rho_{plasma}$ is the density of the plasma.

* * * * *